(12) United States Patent
Lewnard et al.

(10) Patent No.: US 7,594,425 B2
(45) Date of Patent: Sep. 29, 2009

(54) METHODS AND SYSTEMS FOR INTEGRITY TESTING OF POROUS MATERIALS

(75) Inventors: John J. Lewnard, Westford, MA (US); Salvatore Giglia, Norwood, MA (US); Mani Krishnan, Nashua, NH (US)

(73) Assignee: Millipore Corporation, Billerica, MA (US)

(*) Notice: Subject to any disclaimer, the term of this patent is extended or adjusted under 35 U.S.C. 154(b) by 136 days.

(21) Appl. No.: 11/545,738

(22) Filed: Oct. 10, 2006

(65) Prior Publication Data

US 2007/0089489 A1 Apr. 26, 2007

Related U.S. Application Data

(60) Provisional application No. 60/725,238, filed on Oct. 11, 2005, provisional application No. 60/802,457, filed on May 22, 2006.

(51) Int. Cl.
*G01N 15/08* (2006.01)

(52) U.S. Cl. .............................. 73/38; 73/40

(58) Field of Classification Search ............ 73/37, 73/38
See application file for complete search history.

(56) References Cited

U.S. PATENT DOCUMENTS

| | | | |
|---|---|---|---|
| 4,701,861 A | 10/1987 | Kauke | |
| 4,881,176 A | 11/1989 | Kononov | |
| 5,282,380 A | 2/1994 | DiLeo et al. | |
| 5,457,986 A | 10/1995 | DiLeo et al. | |
| 5,581,017 A | 12/1996 | Bejtlich, III | |
| 6,067,844 A * | 5/2000 | Westbrook et al. | ....... 73/40.5 R |
| 6,568,282 B1 | 5/2003 | Ganzi | |
| 6,907,770 B2 | 6/2005 | Von Der Hardt et al. | |
| 2007/0079649 A1 | 4/2007 | Nauseda et al. | |

FOREIGN PATENT DOCUMENTS

DE  19923155 A1  11/2000
EP  0640822 A2  3/1995

OTHER PUBLICATIONS

Phillips and DiLeo, *Biologicals* 24:243, 1996.
Badenhop; Meltzer and Jorritz, *Filtration in the Biopharmaceutical Industry*, Marcel Dekkar, Inc., New York, N.Y., 1998.
R. Prud'homme; T. Chapman, and J. Bowen, *Applied Scientific Research*, 43:6, 1986.
European Search Report, EP 1775015 A1.

* cited by examiner

*Primary Examiner*—Hezron Williams
*Assistant Examiner*—Mark Shabman

(57) ABSTRACT

The invention relates to integrity testing of porous material using a plurality of gases and to an apparatus and system for performing the same.

26 Claims, 15 Drawing Sheets

Figure 15 a
Figure 15 b
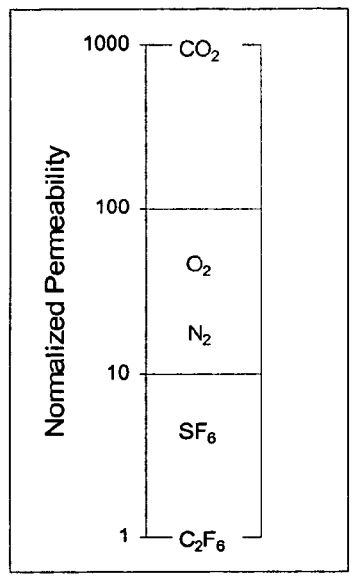
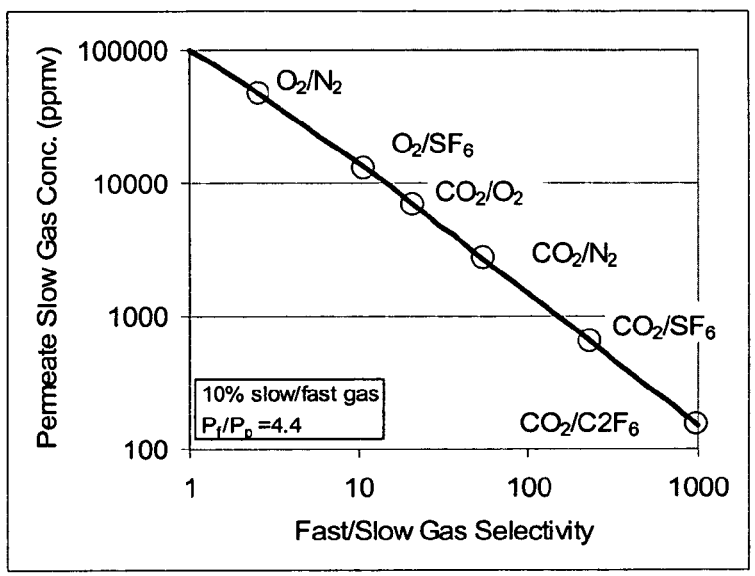

US 7,594,425 B2

METHODS AND SYSTEMS FOR INTEGRITY TESTING OF POROUS MATERIALS

CROSS REFERENCE TO RELATED APPLICATIONS

The present provisional patent application is related to U.S. Provisional Patent Application No. 60/725,238, filed on Oct. 11, 2005 and U.S. Provisional Application 60/802,457 filed on May 22, 2006 both of which are hereby incorporated by reference in their entirety.

FIELD OF THE INVENTION

The invention relates generally to the field of validation testing. In specific embodiments the invention relates to integrity testing of porous materials.

BACKGROUND OF THE INVENTION

Porous materials play a significant role in a wide variety of industrial applications including processing, e.g. filtering, packaging, containing, and transporting manufactured goods and raw materials. The industrial settings in which they are used include the pharmaceutical and biotechnology industries; the oil and gas industries and the food processing and packaging industries, to name but a few.

In several of these industries such as the pharmaceutical and biotechnology industries and the food processing industry porous materials, e.g. membranes, may be used as filtration devices to eliminate undesirable and potentially harmful contaminants from marketable end products. Quality control and quality assurance requires that these filtration devices comply with desired performance criteria. Integrity testing provides a means for ensuring that a particular device meets its desired performance criteria. Typically, in the case of membranes, integrity testing ensures that the membrane is free of defects, e.g. breaches in the membrane exceeding a desired size limitation, which would impair the membrane function and thus allow the end product to become contaminated with harmful or undesirable material.

A variety of integrity tests suitable for ensuring the performance criteria of membranes, e.g., filtration devices, have been previously described. These include the particle challenge test, the liquid-liquid porometry test, bubble point test, the air-water diffusion test and diffusion tests measuring tracer components (see, e.g., U.S. Pat. Nos. 6,983,505; 6,568,282; 5,457,986; 5,282,380; 5,581,017; Phillips and DiLeo, 1996, *Biologicals* 24:243; Knight and Badenhop, 1990, 8th *Annual Membrane Planning Conference*, Newton, Mass.; Badenhop; Meltzer and Jorritz, 1998, *Filtration in the Biopharmaceutical Industry*, Marcel Dekkar, Inc., New York, N.Y.). A number of devices suitable for testing the integrity of a membrane have also been described (see, e.g., U.S. Pat. Nos. 4,701,861; 6,907,770; 4,881,176).

The previously described integrity tests have significant shortcomings. The particle challenge test, for example, is destructive and thus can only be performed once on a given specimen. Although it can be used for post-use integrity testing, it is not suitable for pre-use validation, except for validating the performance of a production lot. Lot validation, however, provides little assurance regarding the integrity of individual membranes within a production lot. Moreover, the test procedures and analysis can be difficult and complex. Flow based tests such as the liquid-liquid porometry test and the bubble point test do not provide a direct universal measurement of membrane retentive performance, but instead assess performance based on a correlation between integrity testing data, e.g. gas or liquid diffusion, and membrane retentive performance. Some flow based tests are also limited in their sensitivity, e.g. size detection limit of membrane defects. Additionally flow based tests are limited to single layer membrane devices, thus defects which are present in only one layer of a multi-layered device will not be detectable using these tests.

A need therefore exists for an integrity test that is suitable for any porous material, including, for example, both single layered and multi-layered devices, e.g. devices comprised of membranes and which provides a non-correlative, universal standard for assessing material performance. The test should be fast, sensitive, non-destructive, inexpensive and easy to execute. It would also be useful to be able to characterize a defect, e.g. by size or density, to determine if a desired performance criteria of the porous material has been compromised as a result of the defect or if the defect is inconsequential in terms of performance criteria. A need also exists for a device and system which can implement such a test.

SUMMARY OF THE INVENTION

Certain embodiments of the invention provide a method, e.g., a mixed gas test, for evaluating the integrity of a porous material that is fast, sensitive, non-destructive, inexpensive and easy to execute, and also provides a universal criteria for assessing the performance integrity of a porous material. The porous material may comprise a single layered or multi-layered membrane device. Universal criteria, as used herein, means that the test result provides a direct measurement of performance criteria that is not dependent on correlation or extrapolation of porous material properties. The resulting value obtained from the test is thus independent of these properties. Thus in some embodiments the invention provides a method of integrity testing of porous materials that is based on the concentration of one or more gases in the permeate of a porous material. In certain embodiments the test is a binary gas test, i.e. dependent on two gases, however more than 2 gases are also contemplated. The test may be independent of flow properties through the porous material. Other embodiments of the invention provide a method for characterizing a defect in a porous material, e.g. by size or density, to determine if a desired performance criteria of the porous material has been compromised as a result of the defect or if the defect is inconsequential in terms of performance criteria. Still other embodiments provide a device and a system which can implement these integrity tests.

In one embodiment the invention provides a method of assessing the integrity of a porous material comprising a) wetting the porous material with a liquid; b) contacting a first surface of a porous material with a mixture comprising two or more gases where at least one of the gases has a different permeability in the liquid when compared to the other gases in the mixture; c) applying pressure to the first surface of the porous material; d) assessing the concentration of at least one of the gases in an area proximal to a second surface of the porous material. The method may optionally further comprise e) comparing the assessed concentration in d) with a predetermined concentration, wherein a difference in the assessed concentration in d) and the predetermined concentration indicates the porous material is not integral.

The predetermined concentration may be, for example, the concentration of gas calculated to diffuse through the integral, wetted porous material at a given temperature and pressure. Integral, when referring herein to a porous material, means non-defective. The given temperature and pressure may be the temperature and pressure under which the test is conducted.

In another embodiment the invention provides a method of assessing the integrity of a porous membrane comprising a) wetting the porous material with water; b) contacting first surface of the membrane with $CO_2$; c) contacting the first surface of the membrane with a hexafluoroethane; d) applying pressure to the first surface of the porous material; e) assessing the concentration of the hexafluoroethane in an area proximal to a second surface of the membrane; and f) comparing the assessed concentration in e) with a predetermined concentration of the hexafluoroethane, wherein an assessed concentration of hexafluoroethane exceeding the predetermined concentration indicates the membrane is not integral.

In still another embodiment the invention provides a method of assessing the integrity of a porous material comprising at least one defect, wherein the method comprises a) wetting the porous material with a liquid; b) contacting a first surface of a porous material with a mixture comprising two or more gases where at least one of the gases has a different permeability in the liquid when compared to the other gases in the mixture; c) applying pressure to the first surface of the porous material; d) increasing the concentration of pressure applied in c) over time; e) assessing the concentration of at least one of the gases in an area proximal to a second surface of the porous material; g) calculating the defect density; h) calculating the defect diameter; i) determining a defect size distribution; and j) comparing the defect size distribution with a predetermined retention value for the porous material, where a defect size distribution greater than the predetermined retention value indicates that the porous material is not integral. The retention value may be for example, the log retention value (LRV).

In yet another embodiment the invention provides a method for finding at least one defect in a porous material comprising a) wetting the porous material with a liquid; b) contacting a first surface of a porous material with a mixture comprising two or more gases where at least one of the gases has a different permeability in the liquid when compared to the other gases in the mixture; c) applying pressure to the first surface of the porous material; d) assessing the concentration of at least one of the gases in an area proximal to a second surface of the porous material; and e) comparing the assessed concentration in d) with a predetermined concentration, wherein a difference in the assessed concentration in d) and the predetermined concentration indicates the porous material has at least one defect.

In a further embodiment the invention provides a method of characterizing a defect in a porous material comprising a) wetting the porous material with a liquid; b) contacting a first surface of a first layer of porous material with a mixture comprising two or more gases where at least one of the gases has a different permeability when compared to the other gases in the mixture; c) applying pressure to the first surface of the porous material; d) increasing the pressure applied in c) over time; e) assessing the concentration of at least one of the gases in an area proximal to a second surface of the porous material; and f) calculating the defect density in the porous material thereby characterizing the defect in the porous material.

In another embodiment the invention provides a method of characterizing a defect in a porous material comprising a) wetting the porous material with a liquid; b) contacting a first surface of a first layer of porous material with a mixture comprising two or more gases where at least one of the gases has a different permeability when compared to the other gases in the mixture; c) applying pressure to the first surface of the porous material; d) increasing the pressure applied in c) over time; e) assessing the concentration of at least one of the gases in an area proximal to a second surface of the porous material; and f) calculating the diameter of the defect in the porous material thereby characterizing the defect in the porous material.

In yet another embodiment the invention provides an apparatus for assessing the integrity of a porous material comprising a) a gas source; b) a gas feed pressure regulator; c) a porous material sample contained in a feed chamber; and d) a permeate sampling port. The apparatus may optionally further comprise at least one of the following: e) a feed sampling port; f) a permeate pressure measuring device; g) a feed pressure measuring device h) a gas-liquid contactor for saturating the feed gas; i) a purge valve on a the feed chamber; j) a permeate gas flow meter; k) a device for measuring the purge gas flow rate; l) a device for measuring the feed gas flow rate; m) and a thermometer for measuring the permeate gas stream temperature and water temperature.

In still another embodiment the invention provides a system for assessing the integrity of a porous material comprising a) a gas source; b) a gas feed pressure regulator; c) a porous material sample contained in a feed chamber; d) a first and second gas; e) a liquid and f) a device for measuring the concentration of at least one gas. The system may optionally further comprise at least one of the following: g) a feed sampling port; h) a permeate pressure measuring device; i) a feed pressure measuring device j) a gas-liquid contactor for saturating the feed gas; k) a purge valve on a the feed chamber; a permeate gas flow meter; l) a device for measuring the purge gas flow rate; m) a device for measuring the feed gas flow rate; and a thermometer for measuring the permeate gas stream temperature.

In further embodiments the invention provides a method of assessing the integrity of a multi-layered device comprising more than one layer of porous material, wherein each layer is comprised of a first and a second surface, and wherein a sample applied to the device will flow from the first surface of the porous material through the porous material to the second surface and where the method comprises a) wetting the porous material with a liquid; b) contacting a first surface of a first layer of porous material with a mixture comprising two or more gases where at least one of the gases has a different permeability when compared to the other gases in the mixture; d) applying pressure to the first surface of the first layer of the porous material; e) assessing the concentration of at least one of the gases in an area proximal to a second surface of a last layer of porous material; and f) comparing the assessed concentration in e) with a predetermined concentration, wherein a difference in the assessed concentration in e) and the predetermined concentration indicates the porous material is not integral.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIGS. 15a and b shows permeabilities of various gases.

DESCRIPTION OF THE EMBODIMENTS

Methods of the Invention

Figure 1:
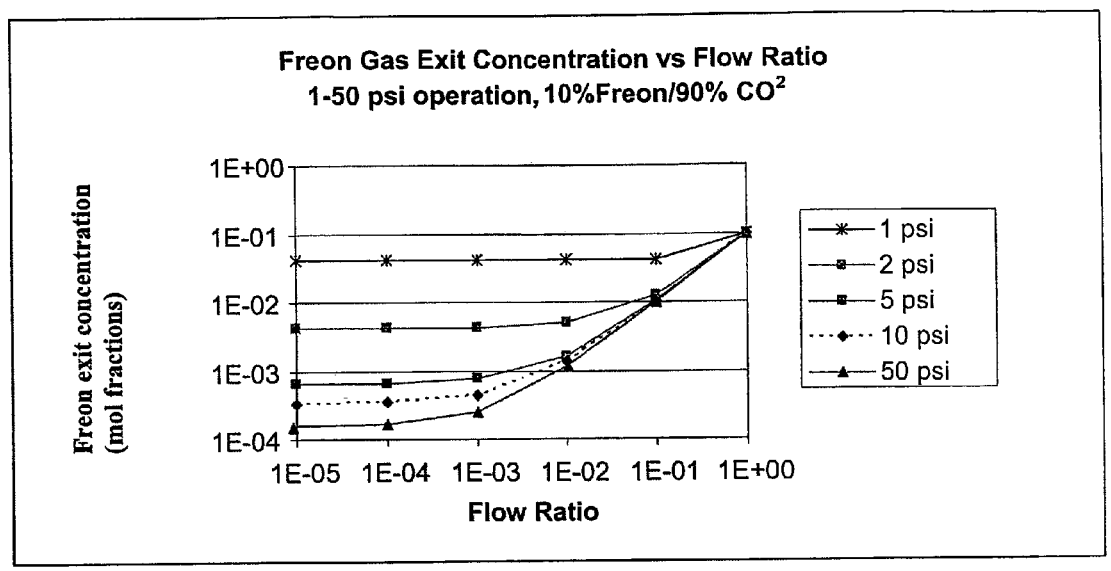
FIG. 1 is a graph showing the hexafluoroethane gas exit concentration versus the flow ratio.

Certain embodiments of the invention provide a method, e.g., a mixed gas method, such as the binary gas test, for assessing the integrity of a porous material. The test relies on measuring the concentration of at least one of the gases in the permeate of a porous material. The binary gas test uses 2 gases with differing permeabilities in a liquid used to wet a porous material. Other embodiments provide for a test which uses a plurality of gases where at least two of the gases have differing permeabilities in a liquid used to wet a porous material. As an example, two of gases may be used for directly determining the integrity of the porous material, while a third gas may be used as an internal standard. Other embodiments of the invention provide a system and an apparatus to practice the methods described herein.

The conditions under which the methods of the invention are practiced may be chosen by the skilled artisan. As an example, the methods of the invention may be practiced at a temperature ranging from about 0° C. to about 100° C. In one embodiment the invention is practiced at a temperature of about 20° C. In another embodiment the invention may be practiced at a temperature of about 4° C. The methods of the invention may be practiced at a pressure, e.g., a feed pressure, ranging from about 1 PSI to about 100 PSI. In another embodiment the methods of the invention may be practiced at a pressure of about 30-50 PSI. In one embodiment the methods of the invention may be practiced at a pressure of about 50 PSI. In another embodiment the methods of the invention may be practiced at a pressure of about 30 PSI. In yet another embodiment the methods of the invention may be practiced at a pressure of about 15 PSI. In a further embodiment the invention may be practiced at a pressure that is just below the bubble point of the porous material. In still other embodiments the pressure may be ramped up, e.g., slowly increased by small increments while measuring flow rate and concentration. In yet other embodiments the pressure may be ramped down, e.g., slowly decreased by small increments while measuring flow rate and concentration. The pressure can be ramped up or down in stepwise increments. The stepwise increments can range from 0.5 psi to 100 psi; or from 1 psi to 25 psi; or from 5 psi to 10 psi.

Where a plurality of gases is used the percentage of each gas in the mixture may be chosen by the skilled artisan. As an example, where 2 gases are used the first gas may be used at a percentage volume ranging from about 0.001% to about 99.999%, and the second gas may be present at a percentage volume ranging from about 0.001% to about 99.999%.

1. Improvements Provided by Certain Embodiments of the Invention

In certain embodiments the invention provides a method of assessing the integrity of a porous material comprising filling, e.g., saturating, the porous material with a liquid and challenging the porous material by increasing the pressure of a multi-component gas feed while measuring the steady state gas composition of the permeate. In other embodiments, e.g., where the device is a multi-layered device, a steady state may not be reached, but a quasi steady state may be attained. In a quasi steady state the concentration changes slowly with respect to time thus permitting measurement of the gas composition concentration. Data points may be obtained at a single pressure point once steady state is achieved or at multiple pressure ramping points as described below. The skilled artisan will understand that in practicing the invention test variables such as operating pressure, solvent, gas species and gas composition may be varied to meet material requirements, sensitivity limits, and operator convenience. It will also be understood by the skilled artisan that functional properties, e.g. retention of a target species such as a virus, may be correlated with integrity measurements made in accordance with the methods disclosed herein.

In some embodiments of the invention a wetted porous material is contacted with a first and second gas where the first and second gas each has a different permeability in the liquid used to wet the porous material. Knowing the composition of the first and second gas and the liquid, a skilled artisan can readily predict the composition of the gas mixture that would permeate through the wetted porous material assuming the material is integral. Pressure may then be applied to the porous material such that potential defects in the porous material are no longer occupied by liquid thus permitting a rapid influx of the gas mixture and a change in the permeate gas mixture compared to the predicted value of the composition of the gas mixture. In some embodiments the steady-state concentration of the less permeable gas may be observed to be greater than its predicted value. Thus, the methods of the invention are not dependent on the resident time a gas spends in a porous material nor are the methods of the invention dependent on flow properties of the porous material. In some embodiments the composition of the gas mixture found in the permeate may be used to assess the integrity of the porous material. Consequently, the test is insensitive to each of the following: small variations in operating pressure, physical properties of the porous material; volumetric changes in the membrane or test housing. In certain embodiments the invention provides a method of assessing integrity of a porous material, e.g. a membrane that is independent of specific characteristics of the membrane such as porosity, tortuosity, and thickness of the wetting fluid. The invention thus provides, in some embodiments, a universal a priori standard for assessing integrity of a porous material.

In certain embodiments the invention provides a method of assessing the integrity of a porous material, e.g., a membrane, which is simple, rapid, repeatable and non-destructive. The method may be performed before or after the porous material is used for its intended purpose and may be repeated more than once, if desired. The method allows the artisan to choose the combination of liquids, gases and porous materials depending on individual need. Moreover, the method increases the sensitivity of assessing integrity compared to previously described methods. Thus certain embodiments of the invention provide a method of detecting defects that are 1-100, 2-50, 10-50 times smaller than the defects detected by air-water diffusion tests.

For many porous materials, e.g., membranes, filter devices, it may be useful to assess the effect of defects on the retentive properties of the material. When it is desirable to quantify defect size and/or defect population density the method of the invention may be practiced in pressure ramping mode such that a plurality of data points are measured as pressure is increased, including for example permeate flow rate. Additional embodiments provide methods for quantifying defect as a function of size. Thus certain embodiments of the invention provide a method of identifying and quantifying defects in the range of 200 nm-2,000 nm, 200 nm-10,000 nm, 10 nm-10,000 nm. The skilled artisan will appreciate that detection ranges will be influenced by filter area, choice of gases, wetting fluid, test pressure and type of detector used.

2. The Universal Standard

As discussed above, one advantage of the methods of the invention, e.g., the mixed gas test, over the air-water diffusion test is its invariance to many test and material properties. As a result, it can provide a universal standard for assessing membrane integrity. For a saturated material, the gas components diffuse through the liquid-filled pores from the high-pressure feed side to the low-pressure permeate side. The diffusive molar flux $n_i$ for component i is given by Fick's law, which for a symmetric membrane is $$\dot{n}_i = \frac{\varepsilon D_i S_i (y_{i,f} P_f - y_{i,p} P_p)}{\tau t} \quad (1)$$

where $\varepsilon$ is the porosity; $D_i$ and $S_i$ are the diffusion coefficient and solubility coefficient, respectively, for gas component i in the liquid filling the material pores; $y_i$ is the mole fraction of gas component i; subscripts f and p refer to the feed and permeate streams, respectively; $\tau$ is the tortuosity of the pores; and t is the thickness of the fluid layer through which components must diffuse. Note that the thickness of the fluid layer is not always equal to the thickness of the material. For example, a pleated membrane may have a liquid meniscus between pleats creating a fluid layer thickness that is greater than the membrane thickness.

Using the equation above for molar flux, it is straightforward to show that the composition of the permeate gas (i.e. the ratio of the fluxes), is independent of porosity, tortuosity, and thickness of the water layer for a defect-free membrane. It is also apparent to one skilled in the art that the molar flow rate (i.e. the product of molar flux and area) will depend on each of these variables. Molar flux, which is the basis for the air-water diffusion test, shows variations with time as a result of pleat deformation and movement, water drainage from membrane pores, and other factors that influence molar flux, but are independent of the inherent integrity of the filter. The air water diffusion test results will also vary with changes in the membrane properties such as porosity and tortuosity. In contrast, the methods described herein, e.g., the mixed gas test, provide results based on the gas composition. The results therefore are invariant with respect to variables for an integral membrane. Consequently one advantage of the methods of the invention is that they provide a single-point measurement to assess porous material integrity which is universal for all materials, and is invariant with fluid drainage issues. This fact can greatly simplify the testing and certification of material integrity.

3. Quantifying Defect Size and Density Distribution

As discussed above, it may be desirable in certain situations to be able to characterize a defect or defects in a porous material beyond merely noting its presence or absence. Certain embodiments of the invention provide a method of calculating defect diameter and distribution density, both of which may be useful in assessing a material's integrity, particularly as it relates to retention.

Gas flow through a defect is due to convective rather than diffusive transport. Several researchers have modeled gas flow in defects assuming the Hagen-Poiseuille equation applies. However, one skilled in the art will recognize that this equation is valid only at the limit of very low pressure differentials across the membrane (R. Prud'homme, T. Chapman, and J. Bowen, 1986, *Applied Scientific Research,* 43:67, 1986.). At typical integrity test conditions, e.g., generally exceeding 20 psi (pounds per square inch), the flow through a defect more closely follows choke flow, particularly if the defect diameter is large relative to the thickness of the retentive zone within the membrane. In general, the transition from Hagen-Poiseuille flow to turbulent flow to choke flow is a function of the ratio of the permeate pressure to the feed pressure. The transition to choke flow, when frictional losses are negligible, occurs when the critical pressure ratio is reached, which depends on the parameter k, the ratios of specific heats, and is a property of the gas components:

$$P_{cr} = \frac{P_p}{P_f} = \left(\frac{2}{k+1}\right)^{\frac{k}{k-1}} \quad (2)$$

For common gases used in integrity testing of porous materials, the transition to choke flow occurs when the feed pressure exceeds about 15 psig and the downstream pressure is ambient. Consequently defect flow discussed by some previous authors describing integrity testing is likely in the choke-flow regime.

It is recognized in the art that defects in a liquid-filled porous material will open when gas pressure forces exceed the capillary force holding the liquid in the pores. The relationship between the defect diameter and the pressure differential across the material is typically modeled via the Laplace equation:

$$d = \frac{4\gamma\cos(\theta)}{\Delta P} \quad (3)$$

where d is the defect diameter, $\gamma$ is the interfacial tension for the gas and liquid filling the membrane pores, and $\theta$ is the contact angle. As a result, defects of different sizes can be opened by varying the operating pressure of the test. This feature is useful since the retention of a species depends on its size relative to the defect size. One can practice the method described herein at a fixed pressure where the pressure is adequate to open all defects larger than the retained species, thereby assessing the impact of defects on retention. Alternatively the test can be run at multiple pressures, allowing defects of different sizes to be opened.

Assuming steady state, uniform upstream and downstream fluid properties, ideal gas, and Henry's law, the composition of the gas at the exit is a function of the operating variables and the flow rate of gas through defect(s) in the membrane device. To simplify the formulation, it is convenient to define the following ratios:

fr=flow ratio=gas flow rate through defects/total gas flow rate
Pr=pressure ratio=permeate pressure/feed pressure
Φ=permeability of gas component i/permeability of gas component j $$\phi = \frac{D_i S_i}{D_j S_j} \quad (4)$$

For a binary gas mixture, these test variables are related by the following quadratic equation:

$$y_{i,p}^2[Pr(1-\Phi)]+y_{i,p}[1-Pr+y_{i,f}(\Phi-1)(1+frPr)+ \\ (1-fr)Pr\Phi]-y_{i,f}\Phi-fr[\Phi y_{i,f}^2-\Phi y_{i,f}-y_{i,f}^2+ \\ y_{i,f}(1-Pr)]=0 \quad (5)$$

By measuring the inlet and outlet gas compositions, it is possible to solve equation (5) to determine the flow ratio. By definition, a membrane with a flow ratio of zero is integral. As noted above, the exit gas composition for an integral membrane (i.e. fr=0) is invariant with membrane properties, and depends on the choice of operating pressures and gas composition. A skilled artisan will recognize that the presence of a defect (i.e. fr greater than zero) will cause the exit concentration to change from the value for an integral membrane. Consequently the composition measurement alone is sufficient to determine if a membrane is integral.

To determine the defect density equation (5) is solved for flow ratio. The Defect flow rate=fr*permeate flow rate. To determine the defect density, it is necessary to use a model for the flow in the defects. As noted above, defect flow can be described as choke flow in many instances for membranes. Differentiating the equations for defect flow with respect to pressure, assuming choke flow, yields defect density according to equation (6):

$$\frac{N_j}{A} = \frac{q_{P_j+\Delta P} - q_{P_j}\left(\frac{P_j + \Delta P}{P_j}\right)}{\left(\frac{P_j + \Delta P}{P_e}\right)\left[\frac{RT}{MW}k\left(\frac{2}{k+1}\right)^{\frac{k+1}{k-1}}\right]^{1/2}} \quad (6)$$

Where $N_j/A$ is the number of pores of size j per area that open as the feed pressure in incrementally increased from $P_j$ to $P_j+\Delta P$; R is the gas constant; T is the temperature; MW is the molecular weight; and other symbols and subscripts are as previously described. Equation (3) can then be used to calculate the defect diameter.

The pressure ratio (Pr) is also an important variable. FIG. 1 shows that the exit concentration varies more rapidly with the flow ratio as the pressure ratio decreases. As a result, the test can detect smaller flow ratios (assuming all defects are opened at the test pressure) as the pressure ratio decreases. The test pressure ratio may be above the critical pressure for the gas, or may be set so that the transmembrane pressure differential is just below the bubble point of the membrane while the pressure ratio is above the critical pressure.

A porous material, such as a membrane, may contain "defects" that do not impact its retention performance where size exclusion is the primary separation mechanism for the membrane. There are several possible reasons why a "defect" would not impact retention. As an example, the defect may be smaller than the species to be retained. Thus the defect not does allow passage of the species. As another example, the defect may be larger than the species to be retained, but the population of defects is too small to impact integrity. Porous materials such as membranes, including filters comprised of membranes, are often designed to remove target species to a specified degree. One standard commonly applied to membranes and filters comprised of membranes is the log removal value (LRV):

$$LRV = -\log_{10}\left[\frac{C_p}{C_f}\right] \quad (7)$$

where C is the concentration of the target species to be retained by the membrane. The defect may reduce the LRV, but still allow the LRV to be within the specified range for the membrane. For example, a virus filter may have a viral clearance guarantee of 4 LRV. Methods of the invention such as mixed gas testing may indicate the presence of defects in the 200-400 nm range. However, if the intrinsic retention of the integral filter is 5 LRV, the defects may only reduce the actual retention to 4.5 LRV, which may still be acceptable. Another advantage of the methods described herein over previously described integrity tests is the ability to quantify the defect concentration as a function of size, so that the impact of a defect(s) on retention can be independently assessed. This allows more discrimination among porous materials that have defects, so that serviceable materials are not erroneously rejected by the integrity test.

Porous Materials

The integrity of any porous material may be assessed using the methods, devices and systems of the invention. As an example, but not as a limitation, the porous material may take the form of a container, a bottle, a cap, a cylinder, a tube, a hose, a cassette, a column, a chip, a bead, a plate, a sheet, or a monolith.

The porous material may be comprised of an organic or inorganic molecules or a combination of organic and inorganic molecules. The porous material may be comprised of a hydrophilic compound, a hydrophobic compound, an oleophobic compound, an oleophilic compound or any combination thereof. The porous material may be comprised of a polymer or a copolymer. The polymers may be crosslinked.

The porous material may be comprised of any suitable material, including, but not limited to polyether sulfone, polyamide, e.g., nylon, cellulose, polytetrafluoroethylene, polysulfone, polyester, polyvinylidene fluoride, polypropylene, a fluorocarbon, e.g. poly (tetrafluoroethylene-co-perfluoro(alkyl vinyl ether)), poly carbonate, polyethylene, glass fiber, polycarbonate, ceramic, and metals. The porous material may be in the form of a single or multilayered membrane. The porous material may be, for example, a hollow fiber, a tubular format, a flat plate, or spirally wound.

In certain embodiments the porous material may be a membrane, e.g., a filter or filtration device comprising a membrane. The porous material may be capable of excluding solutes based on one or more properties of the solutes, e.g., the size of the solutes. As an example the pores of the material may be too small to allow the passage of a particle of a specific size, e.g., diameter or a particular molecular weight.

The membrane may be contained in a housing e.g., a cylinder, a cassette. The membrane may be a single layered membrane or a multi-layered membrane. The membrane may be a flat sheet, a multi-layered sheet, a pleated sheet or any combination thereof. The membrane pore structure may be symmetric or asymmetric. The membrane may be used for filtration of unwanted materials including contaminants such as infectious organisms and viruses, as well as environmental toxins and pollutants. In some embodiments, where the porous material is comprised of more than one layer, an outlet or port may be provided to obtain samples from the interstitial space or spaces.

Multi-layered Membrane Devices

The invention also provides methods, systems and apparatuses for performing integrity testing of multi-layered devices. Multi-layered devices include devices comprised of more than one layer of porous material, e.g. membranes, which in some embodiments may be configured or contained within a housing or cartridge. The multi-layered device may be comprised of 2, 3, 4, 5 or more layers of porous material. The first layer of the multi-layered device may be the layer which is first contacted by a sample entering the device. The last layer of the multi-layered device may be the layer from which a sample exits the device.

Each layer of the porous material may be comprised of a first and second surface. The first surface may be designated as the surface which is first contacted by a sample entering the porous material and the second surface may be designated as the surface from which the material exits the porous material. In some embodiments the multi-layered device may be comprised of a spacer placed between adjacent or stacked layers of porous materials and which may facilitate integrity testing of the multi-layered device. The spacer may be for example a porous non-woven support.

In other embodiments the multi-layered device is not comprised of a spacer between the multiple layers of porous material, e.g. membranes. In some embodiments, the porous material may be stacked in layers such that the layers are in close proximity to each neighboring layer. In some embodiments the stacked layers may be contiguous with the neighboring layer. Air or gas pockets may spontaneously form between the layers in certain embodiments. In other embodiments, e.g. where at least one layer of the device comprises an asymmetric membrane, air or gas pockets may form within at least one layer of the multilayer device. The air or gas pocket may form in a membrane which is highly porous, such as a microfiltratrion membrane. In certain embodiments multiple layers stacked contiguously with the neighboring layer may advantageously serve to maintain the retentive capability of the device. For example a breach or defect in one layer of a device where the material layers are in close proximity may have minimal effect on retentive capability of the device.

In some embodiments the invention provides a method of integrity testing separately each individual layer of a multi-layered device comprised of porous material. The method may include performing the mixed gas test described herein, e.g., the binary gas test. Multi-layered devices, e.g., comprising multiple membranes, which allow integrity testing of individual layers, is described in a co-pending patent application entitled "Integrity Testable Multi-layered Filter Device" filed this day by Rautio et al. A brief description of integrity testing of individual layers of multi-layered devices is provided below.

Figure 2A:
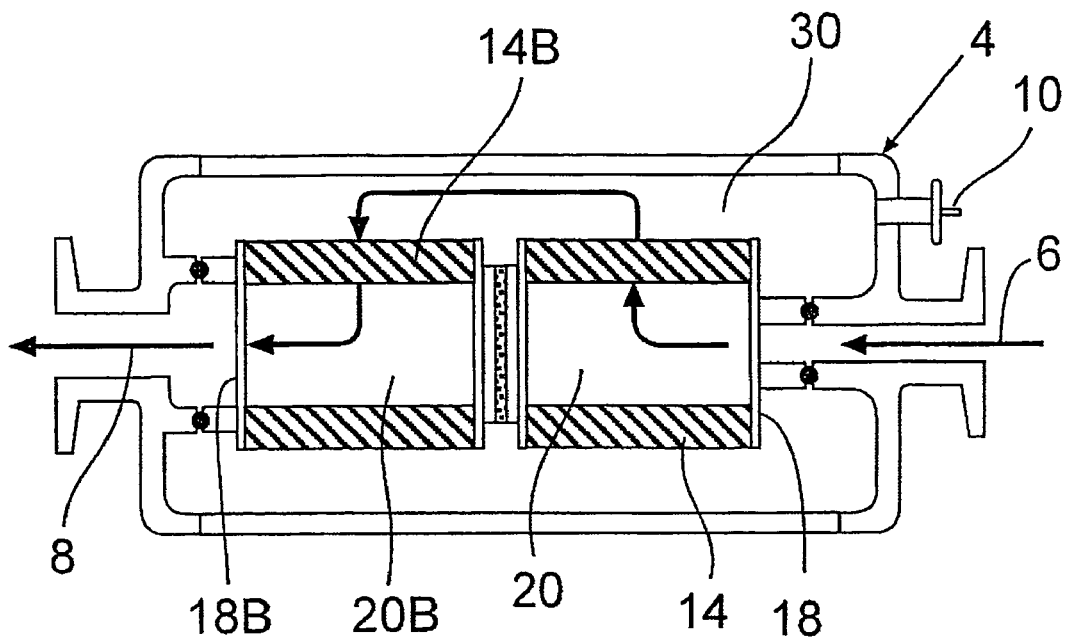
FIGS. 2A, 2B and 2C show examples of a multi-layered membrane used for filtration and integrity testing.

An example of a multi-layered device is shown in FIG. 2*a* which demonstrates normal flow through the device. Fluid enters the inlet 6 into opening 18 of the first layer and then into the core 20. Fluid then passes through the filter element 14 leaving behind any contaminant that the filter is designed to remove by such well-known processes as size exclusion, adsorption, philicity/phobicity or charge repellation. Fluid exits the first element and enters the inner bore of the housing 30. It then enters the second filter layer 14B passing through to the core 20B out through the opening 18B and into the outlet 8 by which it leaves the housing 4. It is understood that 50 represents an impermeable barrier. As with the first layer, fluid passing through the filter element 14B leaves behind any contaminant that the filter is designed to remove by such well-known processes as size exclusion, adsorption, philicity/phobicity or charge repellation. The filter may be the same as the first layer or if desired it may be different in size exclusion characteristics, adsorptive capabilities and the like.

Figure 2B:
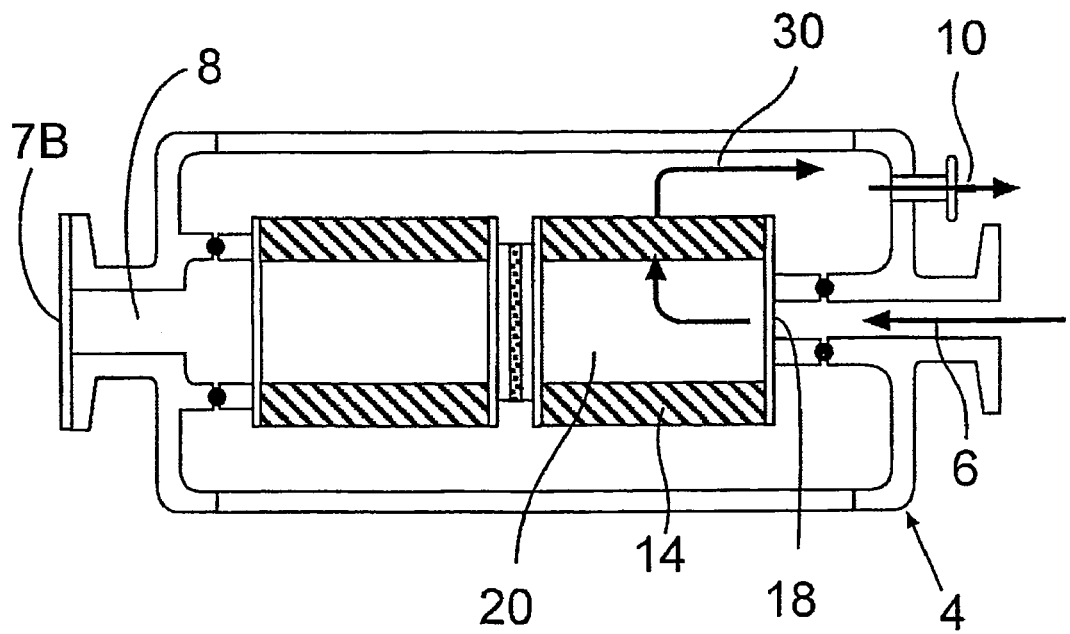

To integrity test the first layer, the set up of FIG. 2B is used. Here the first filter layer 14 is wetted with a suitable liquid for the gas or gases to be used. The outlet 8 is then closed as shown by cap 7B although other means such as a valve (not shown) or the like may be used. The vent 10 is opened and connected to a suitable detection device (not shown). One or more selected gases are flowed through the inlet 6 at a predetermined pressure or series of pressures and the change in flow or gas concentration may be measured by a detection device that has been coupled to the vent 10.

Figure 2C:
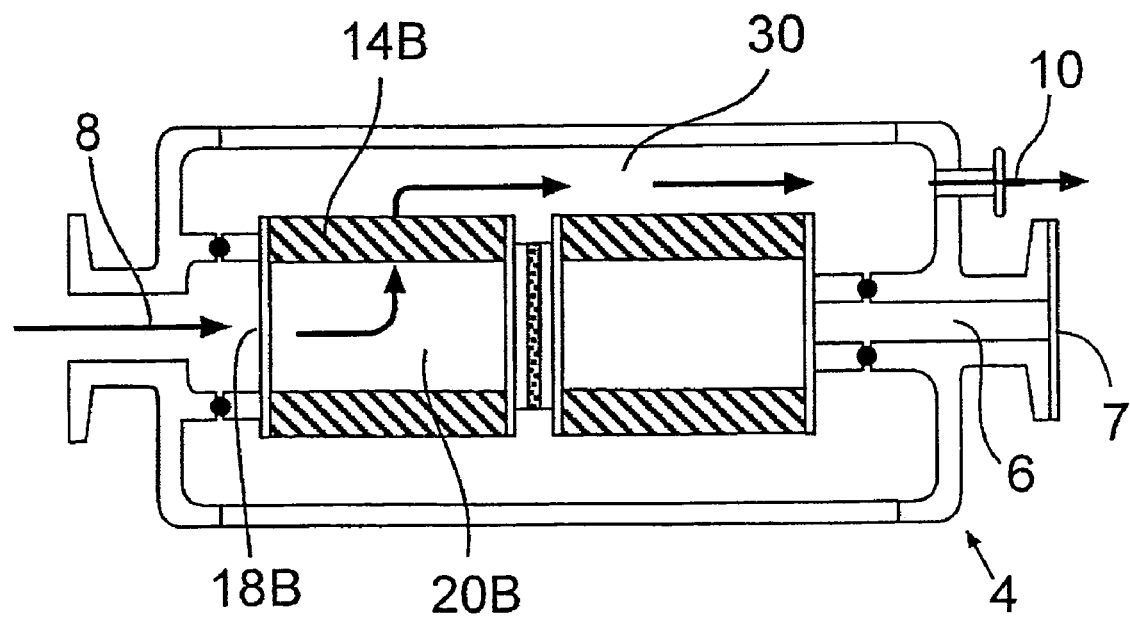

To test the integrity of the second layer 14B, the set up of FIG. 2C is used. Here the second filter layer 14B is wetted with a suitable liquid for the gas or gases to be used. The inlet 6 is then closed (as shown by cap 7 although other means such as a valve (not shown) or the like may be used) and the vent 10 is opened and connected to a suitable detection device (not shown). One or more selected gases are flowed through the outlet 8 at a predetermined pressure or series of pressures and the change in flow or gas concentration is measured by a detection device that has been coupled to the vent 10.

The skilled artisan will appreciate that the device depicted in FIG. 2 may be adapted to provide a sweep gas by the addition of one or more ports and/or tubing.

The invention also provides a method of integrity testing a multi-layered device, e.g. comprised of more than one layer of porous material, e.g., membranes, as a whole unit, i.e. without the need for individually testing each material layer comprising the multi-layered device. Testing a multi-layered device as a whole unit, compared to testing individual layers, allows for a simplified design of the multi-layered device because it does not require special engineering to facilitate integrity testing of each individual layer comprising the multi-layered device.

Figure 12:
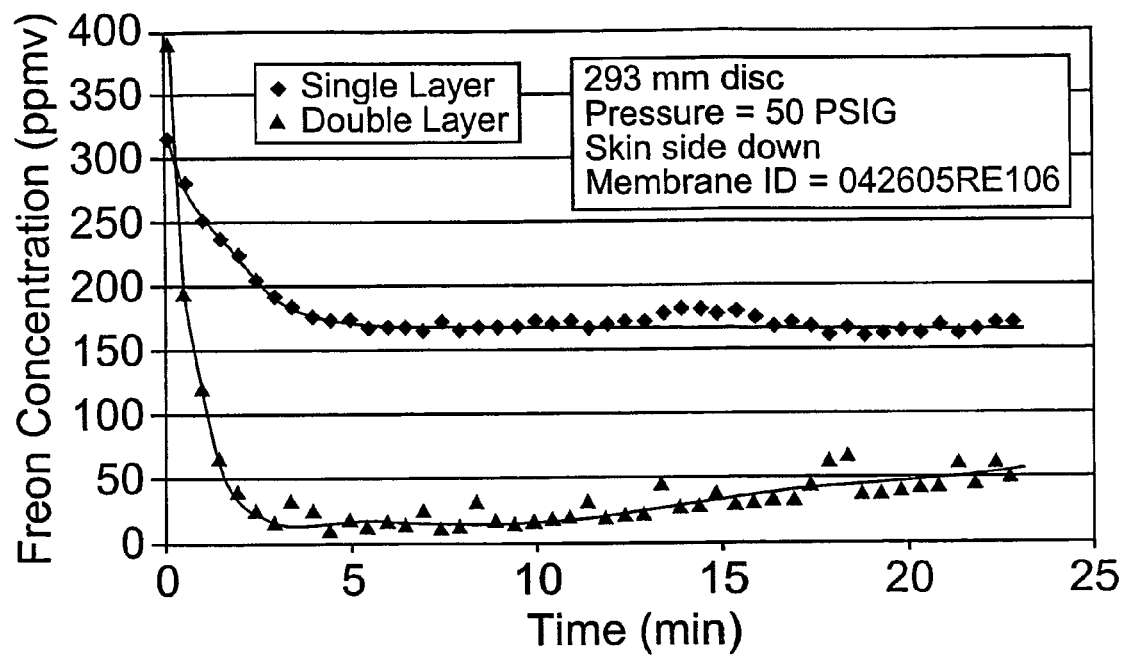
FIG. 12 is a graph comparing hexafluoroethane permeate concentration, as a function of time, for a single layered membrane device and a multi-layered membrane device.

Surprisingly, it has been discovered that the sensitivity of the mixed gas test is increased when a multi-layered membrane device is tested as a unit compared to a single layered membrane tested under identical conditions because smaller amounts of the slower, less permeable gas, are able to penetrate all the layers of the multi-layered device (FIG. 12 and Example 8, infra.). For example, a mixture of gas comprising 90/10 $CO_2/C_2F_6$, or the like, may be used to test a multi-layered device according to the invention. Because less $C_2F_6$ is present, small changes in $C_2F_6$ concentration indicative of smaller or fewer membrane defects will be more readily detected compared to a single layer device. The sensitivity of the mixed gas test is thereby increased and the impact of a defect is more easily discerned. With the binary gas test, a defect is detected because a portion of the feed gas flows into the permeate gas via the defect, in effect contaminating the permeate gas and causing a concentration change. The sensitivity of the test is related to the difference in concentration between the feed gas and the permeate gas when the membranes are integral. Since this difference is accentuated when the membrane is binary gas tested in multi-layer form, the sensitivity of the test in detecting defects is also increased. As a hypothetical example, consider a situation where the permeate flow rate of a 10/90 hexafluoroethane/$CO_2$ gas mixture through an integral single layer membrane is 100 cc/min and the permeate hexafluoroethane concentration is 200 ppmv. If a leak is developed such that 0.01 cc/min of feed gas flows into the permeate, the permeate concentration will increase to 210 ppmv, representing a 5% increase over the integral value. For an integral double layer membrane, in which the Freon concentration is measured to be 50 ppmv (lower than the single layer due, perhaps, to the staging effect due to the gas layer between layers), and which will have a permeate flow rate of about 50 cc/min (half that of a single layer), the same 0.01 cc/min leak of feed gas into the permeate will result in a permeate concentration of 70 ppmv, representing a 40% increase over the integral value. This result is surprising because the permeate composition is independent of the thickness of the membrane material. Without being bound by any particular theory, it is believed the air or gaseous composition separating the layers may contribute to the lower hexafluoroethane levels found in the permeate of the multi-layered membrane device because the gas separation, i.e. of mixed gases used in the integrity test, becomes a multi-stage separation process increasing the extent of separation of the gases in the test mixture.

Liquids

The methods of the invention provide for the use of any suitable liquid to be used as a wetting agent for the porous material. Selection of a wetting agent is within the skill of the artisan and may be determined based on chemical and physical properties of the porous material. Porous materials vary in terms of their wettability, which is often expressed in terms of the contact angle θ. The methods of the invention, e.g., the mixed gas test, can be adapted for hydrophobic membranes, for example, by selecting non-aqueous solvents or prewetting it with low surface tension fluids (such as a mixture of 30% isopropyl alcohol and 70% water) and exchanging the low surface tension fluid with water. The operating pressure can be adjusted by selecting fluids with the appropriate surface tension γ, which generally range form about 74 dyne/cm for water to about 10 for perfluorinated solvents. A skilled artisan will thus understand that a liquid may be selected by considering the chemical properties of the porous material to be tested. As an example where the porous material is comprised of a hydrophilic material a suitable liquid includes water or a solution comprised of water. The solution may be, for example, aqueous solutions containing salts and oxygenated hydrocarbons such as aldehydes or alcohols or neat alcohols such as isopropyl alcohol. Where the porous material is a comprised of a hydrophobic material a suitable liquid may include any organic solvent such as dodecane, perfluorinated compounds, carbon tetrafluoride, hexane, acetone, benzene, and toluene.

Gases

The invention provides for flexibility with regard to choices of liquid and gas components and compositions. In certain embodiments it is desirable to choose gases which have differing permeabilities in the liquid chosen to wet the porous material to be tested. In some embodiments a plurality of gases may be used. Typically the gas which is most permeable in the liquid may be considered the carrier gas. A tracer gas may be used to detect the presence of defects. The tracer gas may be any gas which is less permeable in the liquid than the carrier gas. The test sensitivity can be optimized by selecting gas pairs (in some embodiments) and liquids with proper Φ in the feed composition. In the limit of using a dilute tracer gas, the sensitivity of the gas measurement is a function of the feed composition and Φ.

$$\frac{d y_{i,e}}{d fr} = -\frac{(1 - 1/\phi)(1/y_{i,f} - 1)}{[1 + (1/y_{i,f} - 1)/\phi + fr/y_{i,f}]^2} \quad (8)$$

In general it is useful to choose gas pairs with large differences in permeability and gas compositions that have one species in trace concentration and the other present as the bulk species. For example, Φ can vary from approximately 0.001 to 1 for binary gas mixtures using common species such as nitrogen, oxygen, carbon dioxide, helium, hydrogen, and hexafluoroethane, with water as the pore-filling liquid. For tests with hydrophobic liquids, such as dodecane, gas pairs could include high permeability gases such as ethane, propane, and butane paired with low-permeability gases such as He, $H_2$, and $N_2$. In some embodiments at least one of the gases may be Freon, e.g., hexafluoroethane. In other embodiments at least one of the gases is a noble gas. In still other embodiments at least one of the gases is $CO_2$. In further embodiments at least one of the gases is comprised of a mixture of gases. Where the gases are provided as a mixture of more than one gas, the mixture may be premixed before contacting the porous material. Wide ranges of gas composition are available; for example feed gas mixtures of hexafluoroethane in $CO_2$ can vary from less than 0.1% to more than 99.9%. The skilled artisan will be able to choose appropriate gases and gas mixtures based upon known properties such as permeability (FIGS. 15a and b).

Apparatus and Systems

Figure 3:
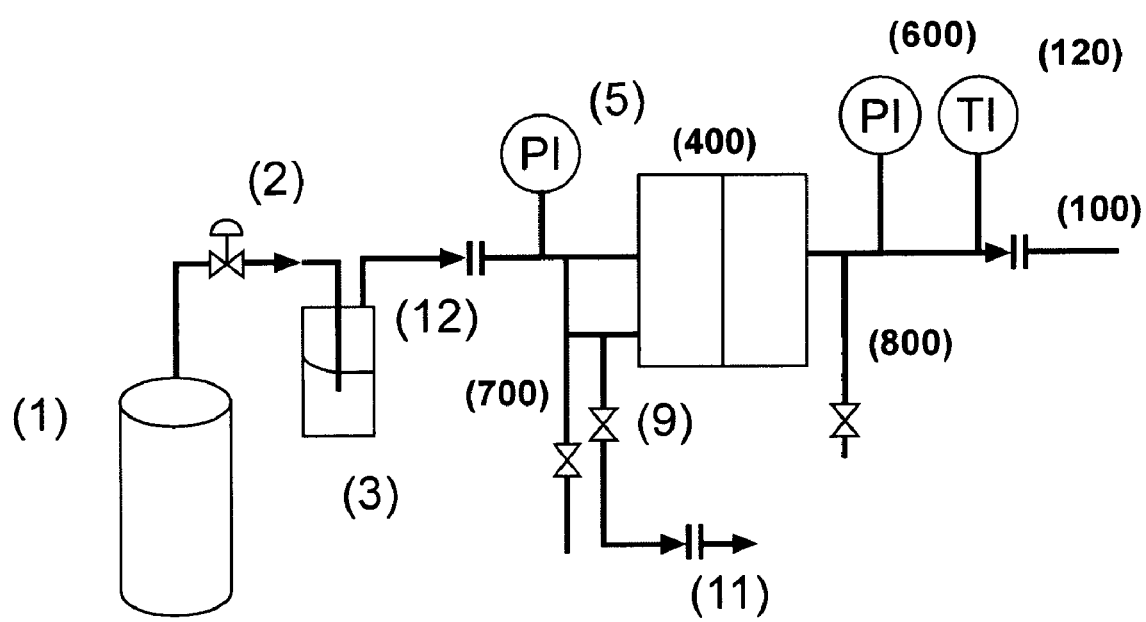
FIG. 3 is a schematic diagram of a device suitable for performing integrity testing of a porous material.

An example of an apparatus suitable for use in the methods of the invention is shown in FIG. 3. The apparatus may comprise a gas source (1) and feed gas pressure regulator (2). Depending on the volatility of the pore-filling solution, it may be desirable to optionally saturate the feed gas in a gas-liquid contactor (3) to prevent premature evaporation of the solution from the membrane sample (400). A feed pressure-measuring device (5) and a permeate pressure-measuring device (600) are optionally provided, and may be useful if permeate pressure is not at atmospheric pressure. The feed (700) and permeate (800) gas compositions are measured at their respective sample points. Depending on the test duration, the surface-to-volume ratio of the test apparatus, and the permeabilities of the gases, it may be advantageous to include a purge valve (9) on the feed chamber to ensure the feed concentration remains constant during the test. If a purge is used, the feed gas sample point may be in the purge stream. If it is desired to calculate the pore density, a permeate gas flowmeter (100) may be used. As an option, the purge gas flowrate (11) and feed gas flowrate (12) may also be measured, or the permeate flow rate can be calculated by measuring the composition of the feed, purge, and permeate gases and any one of the feed gas or purge gas flow rates. The temperature (120) of the filter device should be measured, e.g., in the permeate gas stream using a thermometer.

The invention also provides a system for assessing the integrity of a porous material. The system may comprise the apparatus described above and further comprise a plurality of gases and a sensor device, e.g., a device to sample and/or analyze permeate flow. Choosing a sensor device is well within the capability of the skilled artisan. Suitable sensor devices may include a mass spectrometer, a gas chromatography column, infrared detector, an ultra-violet detector, a Fourier transform infrared detector, a volumetric bubbler/titrator. Since the gas composition can vary over 4 orders of magnitude, it is desirable to use a detector that has a wide operating range. The system may optionally include a computer, e.g. a personal computer. The computer may be used to control automation of the test and may also be used to store and/or analyze data.

The system may optionally include a device suitable for assessing the integrity of a housing which is used to contain a porous material. Housing defects do not necessarily impact the retentive properties of the porous material, e.g. the filter. However, they can result in process fluid leaks, and compromise the overall sterility of the process by providing an ingress route for adventitious contamination. Incorporating a gas detector exterior to the porous material housing facilitates concurrent gas detection for integrity and housing leaks, saving time and equipment An example of a procedure for performing an integrity test of the housing may include the following steps:

1. Saturate the membrane with the pore-filling fluid, and then drain excess fluid.
2. Pressurize the system with feed gas at the minimum test pressure. Note that if test is run at only one pressure, the feed pressure should be set to open all pores large enough to impact retention.
3. Set the purge rate as required to ensure constant feed composition.
4. Measure the steady-state feed gas composition and pressure.
5. Measure the steady-state permeate gas composition, pressure, temperature, and flow rate, as required.
6. Increase the pressure and repeat steps 3-5.
7. Stop the flow, and flush the system to remove gas-saturated fluid.

EXAMPLES

Example 1

Binary Gas Test as a Universal, a Priori Criterion for Integrity

Several membranes were tested using a feed gas containing 10+/−3% hexafluoroethane in $CO_2$. The tests were run at ambient temperature, with a feed pressure of 30+/−5 psig, and a permeate pressure of 0+/−0.5 psig. The feed and exit gas composition was measured by a Cirrus mass spectrometer (MKS, Methuen, Mass.). The hexafluoroethane concentration in the permeate gas for the membranes is listed in Table 1. The integrity of the samples was verified by independent tests.

The membranes were all made by Millipore (Bedford, Mass.) and include 0.22 micron Durapore®, a symmetric membrane made from polyvinylidene fluoride (PVDF), tested in 15 pleated 10-inch cartridge (CVGL); Viresolve® 180, an asymmetric ultrafiltration membrane made from PVDF and tested in 2 flat sheet samples; and an asymmetric ultrafiltration membrane made from polyether sulfone (PES) and tested in 5 flat sheet samples.

These membranes have significantly different structural features such as degree of asymmetry, pore size distributions, thickness, and porosity; permeability; and materials of construction. As predicted by theory, the permeate hexafluoroethane concentrations for different integral membranes all fall within a very narrow range, and is close to the theoretical value predicted based on literature values for hexafluoroethane and $CO_2$ diffusivities and solubilities, with no adjustable parameters.

TABLE 1 hexafluoroethane permeate concentrations for integral membranes and filters

| Membrane | hexafluoroethane concentration, ppm |
|---|---|
| 0.22 micron Durapore ®, 10-inch cartridge | 239 +/− 25% |
| V-180, flat sheet | 261 +/− 5% |
| PES ultrafiltration, flat sheet | 205 +/− 23% |
| Theoretical concentration for range of test conditions | 190–270 ppm |

The methods of the invention described herein, such as the mixed gas test can establish a universal, a priori criterion for membrane integrity. Other integrity tests, such as the air-water test, CorrTest™ and transient measurements of Betjlich rely on correlations between the test measurements and independent retention tests to establish the integrity criterion for the test. The precision of the correlation depends on the inherent variability of the test and membrane materials, and must be revalidated whenever significant changes are made to the membrane or test methods, materials, hardware, etc. With the mixed gas test, the criteria for absolute integrity can be established independent of any specifics regarding the membrane structure, retention test methods, etc. The factors that determine the criterion of membrane integrity are the gas composition, choice of liquid, and pressure ratio.

Example 2

Determination of Defect Size Distribution and Impact on Retention

The presence of a defect resulting in a permeate concentration that differs from the predicted value for an integral membrane may not adversely affect the membrane performance. The mixed gas test allows defects to be quantified in terms of their size and population (number per unit area) and is illustrated in the pressure-ramping method operating mode described in this example.

Two asymmetric ultrafiltration membranes made from PES were cast at conditions that yielded the same pore size distribution, as measured by liquid-liquid porometry. However, the casting conditions varied so that one membrane (201) had defects, while the other membrane (205) was integral. As a result, the two membranes would be expected to have the same virus retention, with the exception of the influence of the defects.

The mixed gas test was performed with water as the pore-filling fluid and 10% hexafluoroethane in $CO_2$ as the feed gas. During the course of the test the pressure was increased from about 20 psi to about 90 psi. The permeate concentration was measured by mass spectrometer, and the permeate flow rate was measured by water displacement. Based on the results, fr was calculated according to Equation 5, and the defect flow rate calculated from Equation (6).

The results of the test for the membrane with defects are shown in table 2 below.

TABLE 2

| Feed pressure (psig) | Permeate Freon Concentration (mole fraction) | Permeate Flowrate (cc/min) | flow ratio (calc) | Defect flow (cc/min) |
|---|---|---|---|---|
| 10 | 4.92E-03 | BLD | 4.66E-02 | 0.00E+00 |
| 21 | 4.03E-03 | BLD | 3.88E-02 | 0.00E+00 |
| 31 | 1.78E-03 | BLD | 1.63E-02 | 0.00E+00 |
| 41 | 2.31E-04 | BLD | 7.34E-04 | 0.00E+00 |
| 62 | 1.68E-03 | 0.74 | 1.56E-02 | 1.15E-02 |
| 73 | 1.69E-02 | 1.88 | 1.69E-01 | 3.18E-01 |
| 81 | 3.66E-02 | 3.26 | 3.69E-01 | 1.20E+00 |
| 91 | 6.93E-02 | 8.2 | 7.00E-01 | 5.74E+00 |

Figure 4:
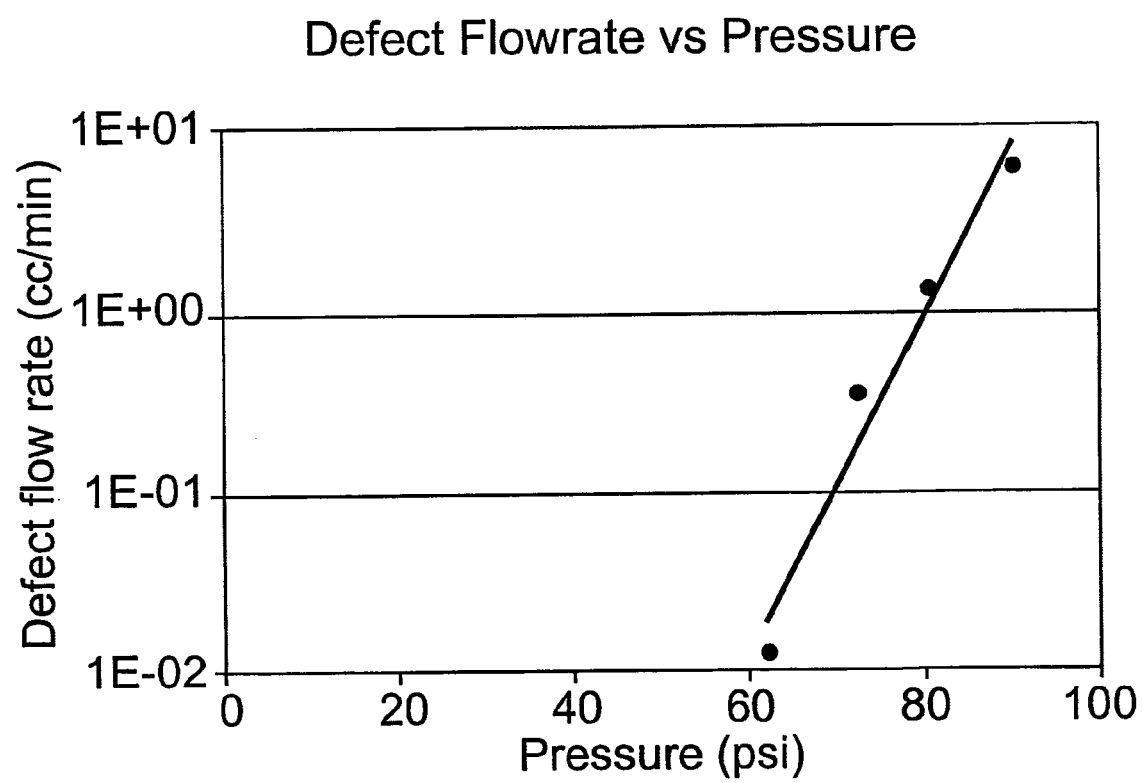
FIG. 4 is a graph showing defect flow rate versus pressure.

The defect flow rate as a function of pressure is shown in FIG. 4 for the membrane with defects; the other membrane was integral and had a defect flow rate less than $10^{-2}$ cc/min. As expected for this type of asymmetric membrane, the defects appear at pressures greater than about 60 psi, suggesting the defects are present in the thin ultrafiltration layer, and terminate in the underlying microfiltration support structure. The defect flow increases exponentially with pressure, suggesting additional defects are continuing to open as the pressure increases.

Figure 5:
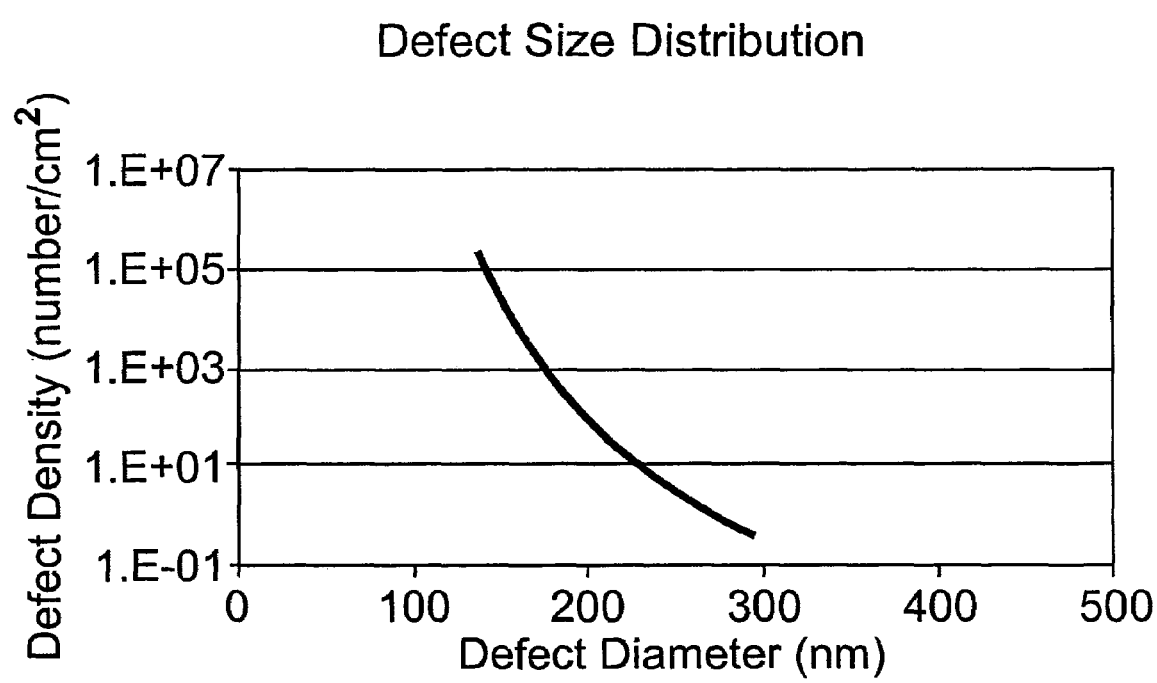
FIG. 5 is a graph showing defect size distribution.

The defect density, or number per area, as a function of pressure is calculated from equation (6). Equation (3) was used to calculate defect diameter as a function of pressure. The defect size distribution (defect density vs. defect diameter) is obtained by combining the results of Equations (3) and (6), and is shown in FIG. 5.

The two membranes were challenged with a buffer solution containing of bacteria phage viruses, $\phi$X-174 (nominally 28 nm in diameter) and $\phi$-6 (nominally 90 nm in diameter). The results are shown in table 3 below. The results demonstrate that the defects present in 201 reduce the membrane's effectiveness, but that the membrane is still fit for its intended use if the target clearance is 4 LRV for $\phi$6. Consequently the fact that the mixed gas test can provide a defect size distribution rather than just a pass/fail result allows it to differentiate among filters with defects.

TABLE 3

| | Measured LRV | | Calculated LRV | |
|---|---|---|---|---|
| Sample | $\phi$X-174 | $\phi$-6 | $\phi$X-174 | $\phi$-6 |
| 205 | 1.6 | 5.1 | | |
| 201 | 1.2 | 4.2 | 1.6 | 3.0 |

The impact of the defects on retention can be calculated a priori using the measured defect size distribution. For virus filtration, where retention is primarily due to size exclusion, the RV is related to the defect size distribution by the following:

$$LRV = -\log_{10}\left(10^{-LRV^*} + \frac{\frac{\pi}{32\tau t}\sum_{j=1}^{m}(N/A_j)d_j^4}{\frac{\pi}{32\tau t}\sum_{j=1}^{m}(N/A_j)d_j^4 + 1/r}\right) \quad (9)$$

where LRV* is the intrinsic retention of the integral membrane and r is the membrane hydraulic resistance, d is the diameter of the defect, and other symbols are as previously described.

Equation (9) is useful because it shows that once the defect size distribution is known, its impact on retention is independent of the solution viscosity, concentration, temperature, etc. Consequently the results from the mixed gas test can be directly applied to a variety of membrane integrity applications where size exclusion is the primary separation mode.

Assuming the retention measured for the 205 membrane is the intrinsic LRV*, the LRV for the 201 membrane is calculated via Equation 9. The results in Table 3 show that the defect distribution has a minimal impact on the retention of $\phi$X-174, but does affect the LRV of the more highly-retained $\phi$-6. The calculated results are in good quantitative agreement with the measured results, showing that the mixed gas test can provide quantitative assessment of the impact of defects on retention.

Example 3

Comparison of Binary Gas Versus Air-water Diffusion Test

The results of this example demonstrate that the mixed gas test has greater sensitivity, and is less susceptible to extraneous test variables, than the air-water diffusion test. Three single layer 3-inch asymmetric PES pleated ultrafiltration filters were made from a single roll of membrane. The filter fabrication technique may introduce defects into the filters. Consequently, the filters would be expected to have the same LRV, with any difference due to random defects introduced during module fabrication. The three filters were wetted with water and tested at three pressures following the air-water diffusion test. The results, shown in the FIG. 6, demonstrated that all three filters had the same air flow rate.

Figure 6:
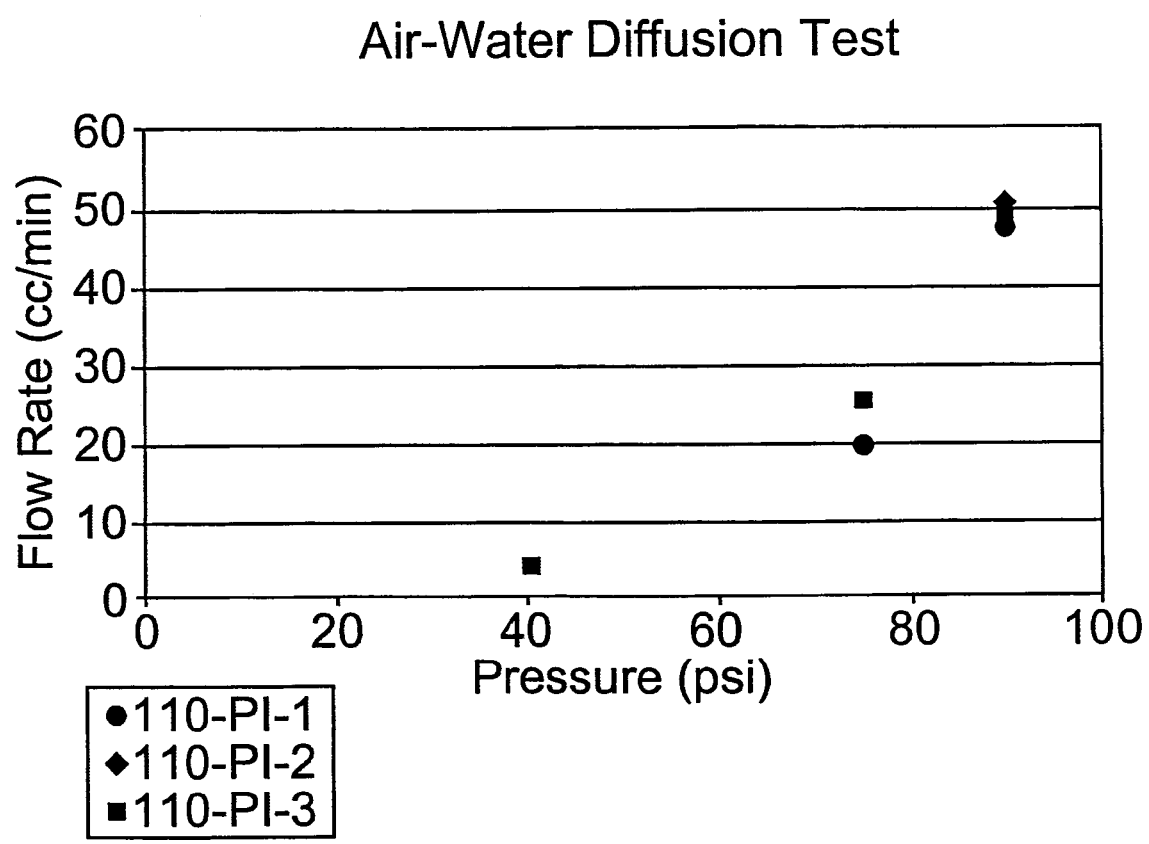
FIG. 6 is a graph showing the results of an air water diffusion test.
Figure 7:
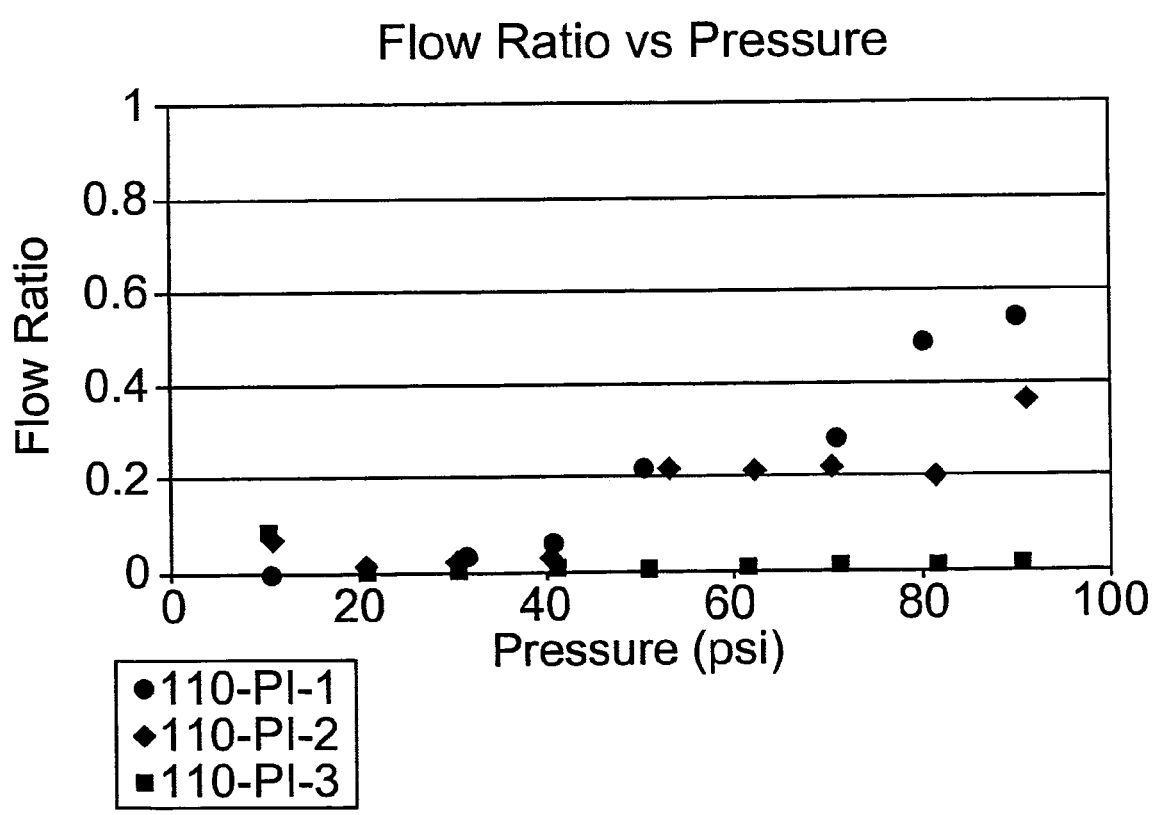
FIG. 7 is a graph showing flow ratio versus pressure.

The three filters were then run with the mixed gas test using 10% hexafluoroethane in $CO_2$ as the feed gas. The flow ratio as a function of feed pressure is shown in FIG. 7. Two filters, 110-PI-1 and 110-PI-2 showed an increase in flow ratio fr above 40 psig, suggesting defects in the ultrafiltration layer. Filter 110-PI-1 had the most defects, while 110-PI-3 had the least. Consequently the mixed gas diffusion test was able to differentiate among the filters, whereas the air-water diffusion test could not (FIGS. 6 and 7).

Following the method of Example 2, the defect size distribution was determined for the three filters. The results, shown in the FIG. 8, demonstrated that 110-PI-1 has about 50% more defects than 110-PI-2, which in turn has 50× more defects than 110-PI-3.

The three filters, and duplicate flat sheet samples of the membrane that were used to make the membrane, were challenged with buffer solution containing IgG and $\phi$X-174. The retention data is shown below in Table 4. The results demonstrate that the defect reduced the retention of all three filters, compared to the retention of the presumptively integral flat sheet sample.

TABLE 4

| Filter | Initial LRV | 75% fouled LRV |
|---|---|---|
| 110-PI-1 | 1.7 | 1.6 |
| 110-PI-2 | 3.6 | 3.0 |
| 110-PI-3 | 5.0 | 4.0 |
| Membrane | 5.4 | 4.7 |

Figure 8:
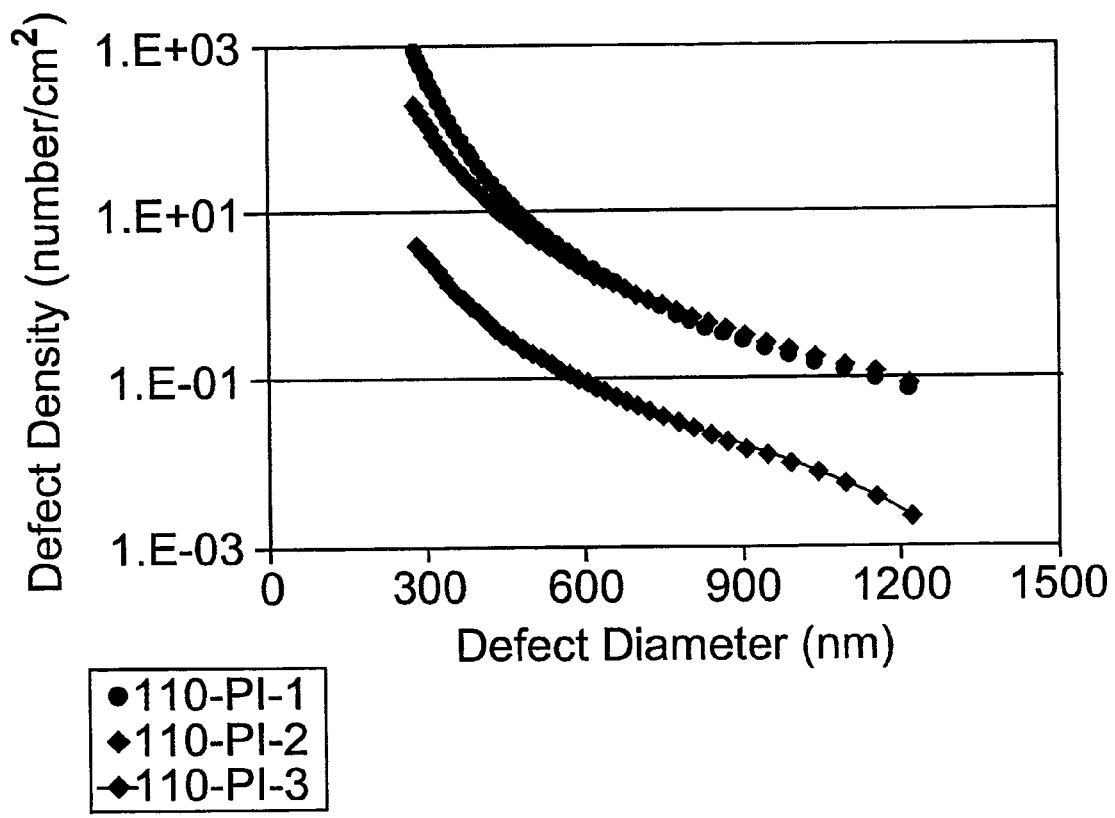
FIG. 8 is a graph showing the estimated defect size distribution of 3 inch PES cartridges.

This example illustrates the sensitivity of the binary gas test. It was able to differentiate the three filters which were indistinguishable by the air-water test (FIG. 6). Further, the binary gas test was able to quantify the defect distribution, showing that defects in filter 110-PI-3 should have a significantly lower impact on LRV than the other filters (FIG. 8).

Example 4

Comparison of Gas Blends

Figure 9:
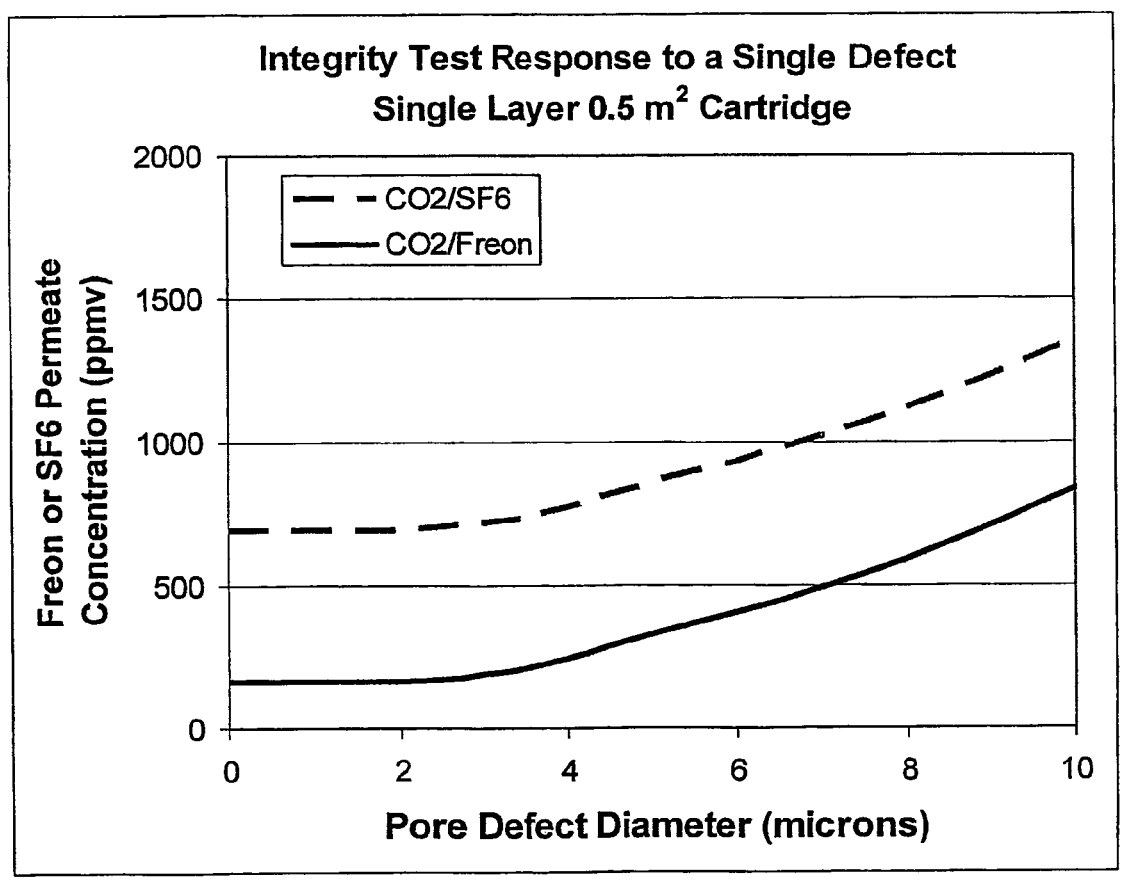
FIG. 9 is a graph comparing binary gas composition using different feed compositions versus defect size.

The flexibility of the mixed gas test can be illustrated by evaluating the sensitivity of the test using alternative gas blends. A symmetric membrane with an intrinsic LRV for two different viruses was modeled using the above equations, and assuming that only a single defect was present. The impact of defect size on permeate concentration is shown in the FIG. 9 for 10% hexafluoroethane/90% $CO_2$ and 10% $SF_6$/90% $CO_2$ at feed pressure of 90 psig and exit pressure of 0 psig. The results show that both trace species will increase in concentration with increasing defect size, although hexafluoroethane is more sensitive for measuring the smallest defects.

Example 5

Correlation Between Viral Retention and Permeate Composition

Figure 10:
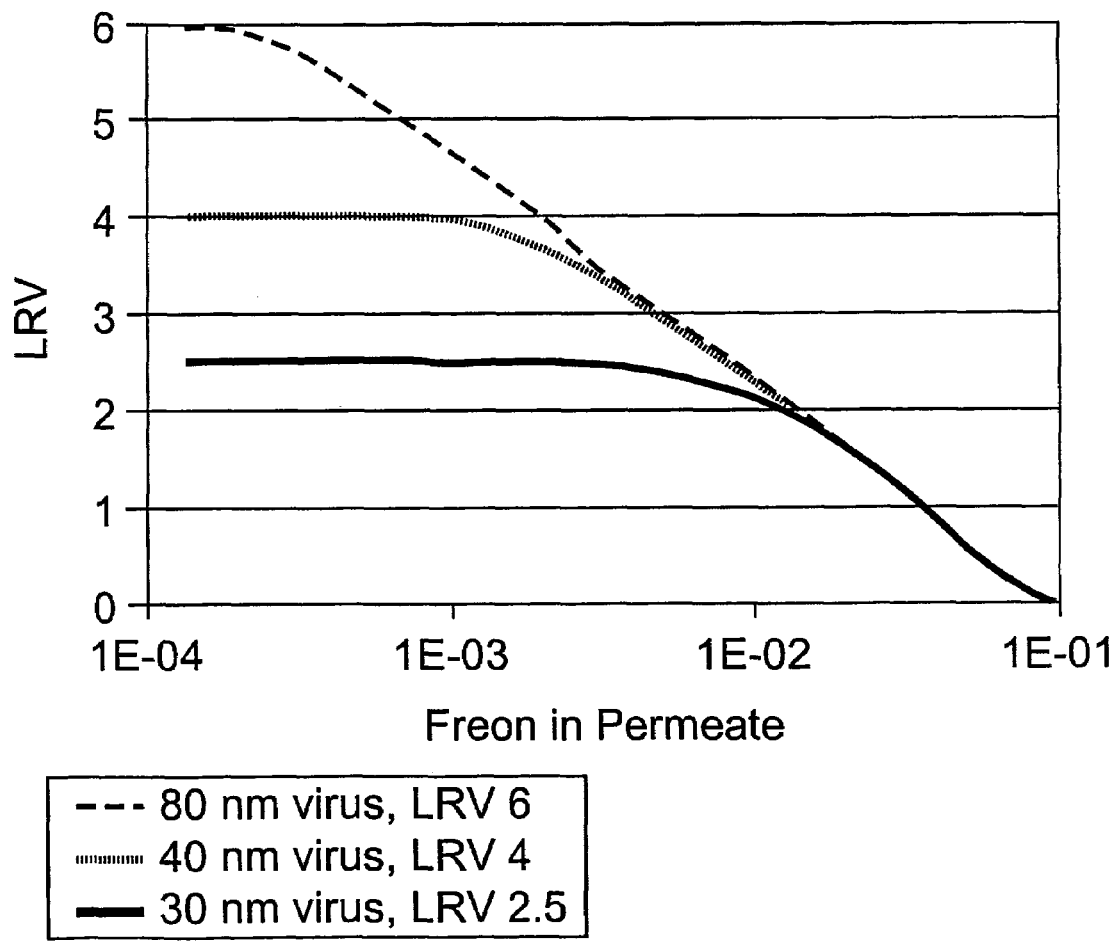
FIG. 10 is a graph showing the log retention value (LRV) versus permeate composition for a 10 inch single layer cartridge.

The utility of the mixed gas test for establishing a correlation between test results (concentration or flow ratio) and retention can be shown with a calculation for a virus filter (FIG. 10). The worst-case scenario for a filter is a single defect of a given size, since the impact of a single defect on retention is worse than the impact of several defects leaking at the same volumetric flow rate. Consequently modeling the mixed gas test with the assumption of a single defect gives the most conservative estimate of the impact on retention. In the calculations, the filter of Example 5 is assumed to have an intrinsic (i.e. defect-free) LRV* of 6, 4, and 2.5 for viruses with diameters 80, 40, and 30 nm, respectively. The permeate composition varies as a result of opening a single defect in the size range of 100 to 2000 nm. At 90 psig feed, the hexafluoroethane concentration for an integral membrane is about 135 ppm. As hexafluoroethane concentration increases to 300 ppm, the LRV of the 80 nm virus species begins to decrease rapidly. The LRV of the 40 nm virus decreases once hexafluoroethane concentration reaches about 1200 ppm. The LRV of the least-retained 30 nm virus is not impacted until hexafluoroethane concentrations exceed 3000 ppm. Using these results, it is possible to construct a "worst-case" correlation between the hexafluoroethane concentration in the permeate and the retention of virus for the filter. One skilled in the art will recognize that similar calculations can be conducted for systems using different liquids (e.g., for hydrophobic membranes); different gases; and different applications (e.g., virus retention, sterilizing filtration).

Example 6

Determination of Defect Size Distribution and Impact on Retention for Viresolve® Membrane The binary gas test method and virus challenge test were conducted on a series of Viresolve® 180 PVDF membranes following the method of Example 2. The membranes were cast under conditions that yielded the same pore size distribution as measured by liquid-liquid porometry, but with varying amounts of defects in the membranes. This membrane is a composite membrane, with an approximately 110 micron layer of microfiltration membrane supporting a thin ultrafiltration layer, less than 5 microns, which accomplishes virus removal. Table 5 (below) shows results for several membranes with increasing number of defects. All samples show a general trend of hexafluoroethane concentration increasing with pressure, indicating defects are opening as pressure increases. A second indication of defects is the increase in the flow ratio, showing a greater proportion of permeate gas is flowing through defects compared to gas diffusing through the integral portion of the membrane. The results show that hexafluoroethane concentration, flow ratio, and defect flow rate correlate with virus retention for operating pressures high enough to open defects (i.e. greater than about 60 psig). In general, the defect flow rate is very low below about 50 psi, and then increases at higher pressure. This result is consistent with defects in the thin ultrafiltration layer. If defects had been present in the microfiltration and ultrafiltration layers, the hexafluoroethane concentration, flow ratio, and defect flow rates would have increased at lower pressures. Consequently the instant technique can provide diagnostic information regarding the location of the defects in the structure. Table 5 follows:

| Sample Number | Phi-X Retention (LRV) | Phi-6 Retention (LRV) | Feed pressure (psig) | Permeate Freon concentration (mol fraction) | Flow Ratio | Defect flow rate (cc/min) |
|---|---|---|---|---|---|---|
| 1 | 2.4 | 5.4 | 12.2 | 4.61E−05 | −2.36E−03 | 0.000 |
|   |     |     | 20.9 | 2.52E−04 | 6.02E−04 | 0.000 |
|   |     |     | 31.2 | 2.69E−04 | 1.11E−03 | 0.000 |
|   |     |     | 40.6 | 3.11E−04 | 1.71E−03 | 0.000 |
|   |     |     | 50.5 | 1.49E−04 | 8.55E−05 | 0.000 |
|   |     |     | 60.5 | 2.90E−04 | 1.63E−03 | 0.000 |
|   |     |     | 71.6 | 4.90E−04 | 3.81E−03 | 0.002 |
|   |     |     | 81.6 | 9.22E−04 | 8.42E−03 | 0.007 |
|   |     |     | 89.9 | 1.49E−03 | 1.45E−02 | 0.014 |
| 2 | 2.1 | 3.2 | 10.1 | 1.19E−04 | −3.42E−03 | 0.00 |
|   |     |     | 19.9 | 5.19E−05 | −2.15E−03 | 0.00 |
|   |     |     | 31.5 | 3.33E−04 | 1.18E−04 | 0.00 |
|   |     |     | 41   | 1.96E−04 | −5.54E−04 | 0.00 |
|   |     |     | 49.9 | 1.74E−04 | −5.85E−04 | 0.00 |
|   |     |     | 60.3 | 2.82E−03 | 1.61E−02 | 0.00 |
|   |     |     | 77.7 | 6.55E−03 | 3.95E−02 | 0.21 |
|   |     |     | 89   | 9.13E−03 | 5.57E−02 | 0.62 |

-continued

| Sample Number | Phi-X Retention (LRV) | Phi-6 Retention (LRV) | Feed pressure (psig) | Permeate Freon concentration (mol fraction) | Flow Ratio | Defect flow rate (cc/min) |
|---|---|---|---|---|---|---|
| 3 | 2.3 | 3.8 | 9.3 | 4.90E−04 | 1.91E−03 | 0.00 |
|   |     |     | 20.3 | 1.65E−04 | −3.03E−04 | 0.00 |
|   |     |     | 31.3 | 2.96E−05 | −1.42E−03 | 0.00 |
|   |     |     | 40.3 | 3.26E−04 | 1.97E−03 | 0.00 |
|   |     |     | 50.1 | 5.64E−05 | −8.91E−04 | 0.00 |
|   |     |     | 62.9 | 3.36E−02 | 3.65E−01 | 0.06 |
|   |     |     | 70.6 | 4.73E−02 | 5.15E−01 | 0.32 |
|   |     |     | 80.2 | 6.63E−02 | 7.22E−01 | 0.59 |
|   |     |     | 90   | 7.33E−02 | 7.99E−01 | 0.75 |
| 4 | 1.5 | 3.8 | 10.4 | 5.73E−04 | 2.74E−03 | 0.0 |
|   |     |     | 21.1 | 8.82E−05 | −1.17E−03 | 0.0 |
|   |     |     | 30.5 | 4.19E−04 | 2.59E−03 | 0.0 |
|   |     |     | 40.7 | 2.46E−04 | 9.55E−04 | 0.0 |
|   |     |     | 50.7 | 2.19E−04 | 7.67E−04 | 0.0 |
|   |     |     | 60.8 | 1.91E−02 | 1.97E−01 | 0.7 |
|   |     |     | 71.5 | 4.38E−02 | 4.54E−01 | 2.6 |
|   |     |     | 80.8 | 5.24E−02 | 5.43E−01 | 3.5 |
| 5 | 1.8 | 3.2 | 11.8 | 0.00046921 | 0.00225458 | 0.0 |
|   |     |     | 20.6 | 0.00066888 | 0.005255329 | 0.0 |
|   |     |     | 29.5 | 0.00034791 | 0.002033512 | 0.0 |
|   |     |     | 41.2 | 0.00016654 | 0.000235508 | 0.0 |
|   |     |     | 50.9 | 0.00034468 | 0.00228985 | 0.0 |
|   |     |     | 60.8 | 0.02722595 | 0.297034591 | 0.0 |
|   |     |     | 71.5 | 0.05364651 | 0.586617774 | 1.9 |
|   |     |     | 81.6 | 0.07960701 | 0.871106879 | 7.0 |
|   |     |     | 91.3 | 0.08907435 | 0.974830662 | 13.2 |

Figure 11:
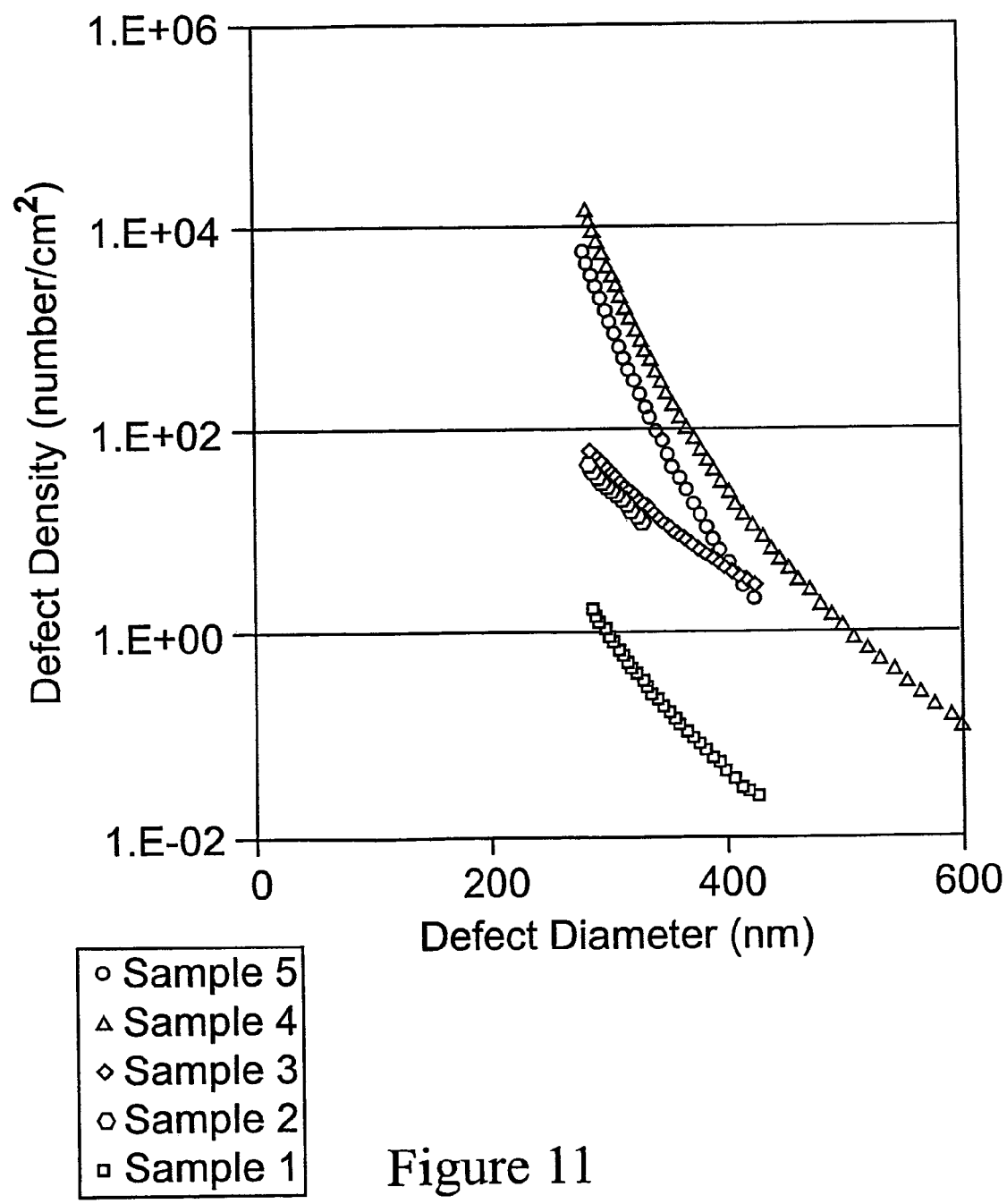
FIG. 11 is a graph showing the defect size distribution for V180 samples.

The defect density as a function of size for the membranes is shown in FIG. 11. The change in defect density correlates to the loss in retention of the φX-174 and φ-6 viruses. The results show that the mixed gas technique can provide both a qualitative ranking for the membranes and a quantitative measure of the defect size and surface population. Further, the ability to define the defect distribution allows discrimination among membranes. For example, Sample 1 has an LRV greater than 5 for φ-6 despite the presence of defects, although retention is lower for the other samples with more and larger defects. Samples 1, 2, and 3 have LRV greater than 2 for φX-174, although the higher defect populations in Samples 4 and 5 decrease their LRV below 2.

Example 7

Integrity Test for Hollow Fiber Modules

The integrity test can be run in different membrane module configurations, including a hollow fiber. A hollow fiber device comprising 9 1.5 mm ID fibers with a nominal pore size of 0.2 microns and a total area of 100 cm² was tested with a feed gas of 10% hexafluoroethane and 90% $CO_2$ at pressures of 11.5, 24.5, and 30.5 psig. At all conditions the flow ratio was greater than 0.5, indicating that the device was not integral.

A second hollow fiber device, model number CFP-2-E-3MA, manufactured by Amersham Bioscience (Piscataway, N.J.), was also tested at pressures between 10 and 23 psig. The device was certified by the manufacturer as integral, with a bubble point of 18-30 psi using a 50:50 ethanol-water mixture. The flow ratio at each pressure was less than 0.005, confirming that the membrane was substantially defect free. The module was then intentionally damaged to introduce a defect, and retested at 10 psig. The permeate concentration and flow ratio both increased dramatically, confirming that the device was no longer integral.

Example 8

Binary Gas Test Comparing Single and Multi-layered Device

A single and double layered polyethersulfone membrane (293 mm diameter disc) were tested using the binary gas test described herein. The double layered membrane did not have a spacer between the layers. Both membranes were prewetted with water and then contacted with a gas mixture comprising 90/10 mole percent $CO_2/C_2F_6$ at 50 pounds per square inch gauge (PSIG). To maintain a constant gas composition on the feed side of the membrane, the integrity test was operated in tangential flow filtration mode with a retentate flow rate of about four times the permeate flow rate. Based on the measured operating conditions and solubilities and diffusivities of the test gases in water, the theoretical permeate concentration of Freon, e.g. hexafluoroethane was calculated to be about 175 ppmv. For the single layer device, the measured concentration was consistent with the theoretical value, however, a lower concentration of Freon was observed for the double layered membrane (FIG. 12).

Since the permeate composition is in theory independent of the liquid thickness, and the membrane layers were adjacent to each other, this result was not consistent with permeation through a continuous liquid path. Thus a gas pocket in between the membrane layers may form, and the gas separation may be divided into a two stage process, resulting in an enhancement of the gas separation. It should be noted that because there was no retentate or removal of gas in between layers, the very low concentration achieved in the permeate was transient. But because of the slow permeation rate of hexafluoroethane, its interlayer concentration buildup was very slow relative to the time scale of the measurements (5-20 minutes). Therefore, in practice the measured concentration of hexafluoroethane in the second layer permeate was several times lower than the value obtained with a single layer and thus provided a means of integrity testing multi-layered devices without the need of engineering septum or sampling ports in between layers.

Example 9

Integrity and Rentention Testing of Single Layered and Multi-layered Devices

Figure 13:
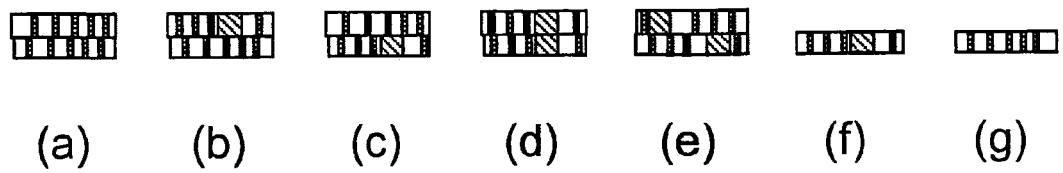
FIG. 13 shows integral and defective single and multi-layered membrane devices. Hatched areas represent pore defects.

A series of tests were conducted on a panel of membrane constructs to compare virus retention performance and binary gas test values of double and single layer devices, with and without defects. The membranes tested were suitable for viral retention applications. Using 90 mm discs (47 cm² effective surface area), a set of integral and defect containing devices were prepared as shown in FIG. 13. The multi-layered membranes were stacked on top of each other. No physical spacer was used to separate the layers, however it is believed a small air spaces spontaneously formed either Within a layer or between layers. FIG. 13(a) shows a two layered integral, i.e. without defects, membrane. FIG. 13(b) shows a two layered membrane having a defect in the top layer (hatched area). FIG. 13(c) shows a two layered membrane having a defect in the bottom layer (hatched area). FIG. 13(d) shows a two layered membrane having coincidental defects in both the top and bottom layers (hatched areas). FIG. 13(e) shows a two layered membrane having offset defects in both the top and bottom layers (hatched areas). FIG. 13(f) shows a single layered membrane having a defect. FIG. 13(g) shows a single layered integral membrane The defects were created using a 1000 μm needle (large enough to cause an essentially complete loss of virus retention) and, except for combination (e) (offsetting defects), centrally located within the disc. For the offsetting defect case, the defects were located about 10 mm from the outside perimeter of the disk and were 180° apart. All the discs were cut from the same PES ultrafiltration membrane material and prepared in duplicate. For this set of devices, two membrane layers were carefully assembled one on top of the other The membrane that was used in these experiments consisted of two sections: a thin ultrafiltration section (commonly referred to as the skin side) and a thicker microfiltration section. The two sections formed a continuous gradient. For the binary gas test, the membranes were tested in both the skin up (ultrafiltration section upstream) and skin down orientations. For the retention test, the membranes were oriented in the skin down direction which is often the preferred orientation for optimum filtration efficiency.

Before retention testing, each device was binary gas tested using a 10/90 Freon/$CO_2$ gas mixture as the test gas. Gas compositions were measured using an MKS model Cirrus LM99 mass spectrometer (MKS, Wilmington, Mass.). The devices were tested at 50 PSIG, with a sweep/permeate flow rate ratio of 4:1. At each test condition, feed pressure, permeate gas flow rate, retentate gas flow rate and permeate gas composition were recorded. The retention test of the devices consisted of permeating 250 ml of a buffer solution containing the bacteriophage φX-174 (approximate diameter of 28 nm) at a concentration of from about $1 \times 10^6$ to $1 \times 10^8$ pfu/ml through the membranes at a constant pressure of 30 PSIG. Assays of the challenge and effluent streams were performed to determine the virus log reduction value (LRV).

Figure 14:
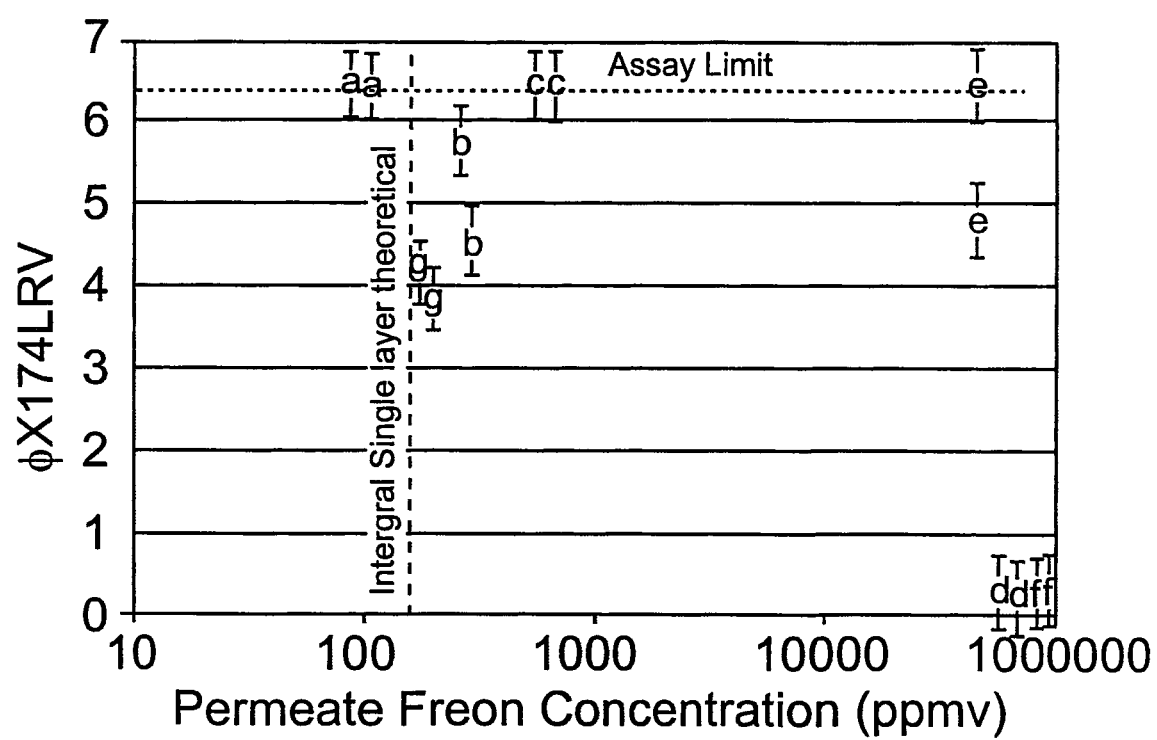
FIG. 14 is graph showing retention versus permeate concentration of various single and multi-layered membrane devices which are either integral or comprised of one or more defects.

The results are presented in FIG. 14. Letters in FIG. 14 correspond to the constructs described above for FIG. 13. As can be seen from FIG. 14, with the use of the binary gas test, an integral double layer device can be differentiated from an integral single layer device and also from a double layer device in which a defect is present in only one of the layers. Furthermore, in the cases where defects were present in only one layer, or where defects were present in both layers but did not overlap or coincide, the impact of defects on virus retention was significantly greater on single layered membranes compared to double layered membranes. This results because when double-layered membranes are tested, the adjoining layer acts as at least a partial blockade of the flow through the defect.

Example 10

Comparison of Binary Gas to Air-water Diffusion Test for a Multi-layered Device

The results of this example demonstrated that the mixed gas test has greater sensitivity, and is less susceptible to extraneous test variables, than the air-water diffusion test. Three double layer asymmetric PES flat sheet ultrafiltration filters, containing either 900 or 1800 cm² of membrane area, were made from a single roll of membrane. The filter fabrication technique may introduce defects into the filters. Consequently, the filters would be expected to have the same LRV, with any difference due to random defects introduced during module fabrication.

Each of the three filters were wetted with water and tested at 30 psig pressure using the air-water diffusion test. The three filters were then run with the mixed gas test using 10% hexafluoroethane in $CO_2$ at 30 psig as the feed gas and with a purge gas to permeate gas flow ratio of 4:1. These three filters, along with three 90-mm diameter disc samples (46 cm² membrane area) of the membrane that were used to make the devices, were challenged with a buffer solution containing IgG and φX-174. Retention values were measured after the membranes had been fouled to the extent that flux had declined by 75% from the initial non-fouled value.

The air diffusion, binary gas, and retention data are shown below in Table 6. The LRV of device no. 2 was not significantly different from the average of the control 90 mm disc samples and is therefore considered integral. Device no. 3 exhibited an LRV that was 0.9 lower than the control discs and device no. 4 showed an LRV that was 0.3 lower than control discs. As shown in Table 6, the air-water diffusion test could not distinguish among the three devices, as all three were measured to have air-water diffusion values in close proximity to each other. The binary test gas values indicated in Table 6 are the measured permeate gas concentrations of hexafluoroethane in parts per million. In contrast to the air-water diffusion test, the binary gas test was able to clearly identify the two devices where the LRV was lower than the control discs. Furthermore, as indicated from the data in Table 6, the binary gas test value showed a clear correlation between the binary gas test value and the deviation from intrinsic membrane LRV of the devices.

TABLE 6

| Filter | Air-Water Flux (cm³/min-m²) | Binary Gas Test Value | 75% Fouled LRV |
|---|---|---|---|
| 90 mm no. 1 | — | — | 5.7 |
| 90 mm no. 2 | | | 5.8 |
| 90 mm no. 3 | | | 5.9 |
| 90 mm Average | — | — | 5.8 |
| Device no. 2 | 12 | 72 | 5.9 |
| Device no. 3 | 11 | 760 | 5.0 |
| Device no. 4 | 12 | 284 | 5.6 |

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims

What is claimed is:

1. A method of assessing the integrity of a porous material comprising:
   a) wetting the porous material with a liquid;
   b) contacting a first surface of a porous material with a gas mixture comprising two or more gases, where at least one of the gases in the mixture has a different permeability in the liquid compared to the other gases in the mixture;
   c) applying a pressure to the first surface of the porous material such that the gas mixture permeates through the porous material;
   d) measuring the steady state concentration of at least one of the gases in the gas mixture permeate in an area proximal to a second surface of the porous material; and
   e) comparing the steady state concentration with a predetermined concentration,
   wherein a difference in the steady state concentration and the predetermined concentration is indicative that the porous material is not integral.

2. The method of claim 1, wherein steady state concentration of the at least one of the gases is measured which is less permeable in the liquid compared to at least one other gas in the mixture.

3. The method of claim 1, wherein the gas mixture comprises a carrier gas, which is the most permeable gas in the mixture.

4. The method of claim 3, wherein the carrier gas is $CO_2$.

5. The method of claim 2, wherein the steady state concentration of hexafluoroethane is measured.

6. The method of claim 2, wherein the steady state concentration of sulfur hexafluoride is measured.

7. The method of claim 1, wherein at least one of the gases is a noble gas.

8. The method of claim 1, wherein the porous material comprises a hydrophilic material.

9. The method of claim 1, wherein the porous material comprises a hydrophobic material.

10. The method of claim 1, wherein the porous material comprises a membrane.

11. The method of claim 10, wherein the membrane is comprised in a filtration device.

12. The method of claim 10, wherein the membrane is an asymmetric membrane.

13. The method of claim 10, wherein the membrane is a symmetric membrane.

14. The method of claim 10, wherein the membrane comprises a polymer.

15. The method of claim 14, wherein the polymer is polyvinylidene fluoride (PVDF).

16. The method of claim 14, wherein the polymer is polyether sulfone (PES).

17. The method of claim 10, wherein the membrane is a flat sheet in flat plate or spiral wound formats.

18. The method of claim 10, wherein the membrane is a pleated sheet, in hollow fiber or tubular formats.

19. The method of claim 1, wherein the liquid comprises water.

20. The method of claim 1, wherein one gas is present at a volume of about 90% and a second gas is present at a volume of about 10%.

21. The method of claim 1, wherein the steady state concentration is measured by mass spectrometer.

22. The method of claim 1, wherein the predetermined concentration is based on the permeability of each of the gases in the liquid.

23. The method of claim 1, wherein the predetermined concentration is based on the diffusion rate of each of the gases in the liquid.

24. The method of claim 1, wherein the porous material is a membrane comprising more than one layer.

25. The method of claim 1, wherein the porous material is selected from the group consisting of polyether sulfone, polyamide, nylon, cellulose, polytetrafluoroethylene, polysulfone, polyester, polyvinylidene fluoride, polypropylene, poly (tetrafluoroethylene-co-perfluoro(alkyl vinyl ether)), poly carbonate, polyethylene, glass fiber, polycarbonate, ceramic, and metals.

26. A method of assessing the integrity of a porous membrane comprising:
   a) wetting the porous membrane with water;
   b) simultaneously contacting a first surface of the membrane with $CO_2$ and hexafluoroethane;
   c) applying a pressure to the first surface of the porous membrane;
   d) measuring the steady state concentration of the hexafluoroethane in an area proximal to a second surface of the membrane; and
   e) comparing the steady state concentration in d) with a predetermined concentration of hexafluoroethane, wherein the steady state concentration of hexafluoroethane exceeding the predetermined concentration is indicative that the membrane is not integral.

* * * * *